United States Patent
Gopinath

(10) Patent No.: US 10,631,754 B2
(45) Date of Patent: Apr. 28, 2020

(54) INTRAVASCULAR ABSORBABLE STENT DETECTION AND DIAGNOSTIC METHODS AND SYSTEMS

(71) Applicant: LightLab Imaging, Inc., Westford, MA (US)

(72) Inventor: Ajay Gopinath, Bedford, MA (US)

(73) Assignee: LIGHTLAB IMAGING, INC., Westford, MA (US)

( * ) Notice: Subject to any disclaimer, the term of this patent is extended or adjusted under 35 U.S.C. 154(b) by 283 days.

(21) Appl. No.: 15/596,723

(22) Filed: May 16, 2017

(65) Prior Publication Data

US 2017/0325712 A1 Nov. 16, 2017

Related U.S. Application Data

(60) Provisional application No. 62/336,931, filed on May 16, 2016.

(51) Int. Cl.
*A61B 5/06* (2006.01)
*A61B 5/00* (2006.01)
(Continued)

(52) U.S. Cl.
CPC .............. *A61B 5/06* (2013.01); *A61B 5/0066* (2013.01); *A61B 5/0084* (2013.01);
(Continued)

(58) Field of Classification Search
None
See application file for complete search history.

(56) References Cited

U.S. PATENT DOCUMENTS 4,548,473 A 10/1985 Lo et al.
5,054,492 A 10/1991 Scribner et al.
(Continued)

FOREIGN PATENT DOCUMENTS

EP 2062526 5/2009
JP 63-127201 5/1988
(Continued)

OTHER PUBLICATIONS

Briguori et al., "Intravascular ultrasound criteria for the assessment of the functional significance of intermediate coronary artery stenoses and comparison with fractional flow reserve," Am J. Cardiol 87:136-141, 2001.
(Continued)

*Primary Examiner* — Samah A Beg
(74) *Attorney, Agent, or Firm* — K&L Gates LLP

(57) ABSTRACT

In part, the disclosure relates to systems and methods of detecting struts in a blood vessel. In one embodiment, an intravascular data collection system and an intravascular data collection probe are used. An exemplary method may include one or more of the following steps converting an image of a blood vessel into an image mask, the image includes struts of a bioresorbable scaffold; inverting the image mask to create an inverted image mask, detecting an insular group of bright/signal containing pixels; and filtering the insular group of bright/signal containing pixels using one or more morphological filters to identify candidate struts; and validating the candidate struts to identify one or more struts of the bioresorbable scaffold.

24 Claims, 23 Drawing Sheets

(51) Int. Cl.
*G06T 7/73* (2017.01)
*A61B 8/12* (2006.01)
(52) U.S. Cl.
CPC ............ *A61B 5/6862* (2013.01); *A61B 5/725* (2013.01); *A61B 5/742* (2013.01); *G06T 7/73* (2017.01); *A61B 8/12* (2013.01); *G06T 2207/10016* (2013.01); *G06T 2207/10101* (2013.01); *G06T 2207/10132* (2013.01); *G06T 2207/30101* (2013.01)

(56) References Cited

U.S. PATENT DOCUMENTS

| | | |
|---|---|---|
| 5,321,501 A | 6/1994 | Swanson et al. |
| 5,459,570 A | 10/1995 | Swanson et al. |
| 5,465,147 A | 11/1995 | Swanson |
| 5,477,858 A | 12/1995 | Norris et al. |
| 5,488,674 A | 1/1996 | Burt et al. |
| 5,509,093 A | 4/1996 | Miller et al. |
| 5,518,810 A | 5/1996 | Nishihara et al. |
| 5,531,227 A | 7/1996 | Schneider |
| 5,586,201 A | 12/1996 | Whiting et al. |
| 5,619,368 A | 4/1997 | Swanson |
| 5,632,767 A | 5/1997 | Sinofsky |
| 5,643,253 A | 7/1997 | Baxter et al. |
| 5,662,109 A | 9/1997 | Hutson |
| 5,715,827 A | 2/1998 | Corl et al. |
| 5,748,598 A | 5/1998 | Swanson et al. |
| 5,771,895 A | 6/1998 | Slager |
| 5,784,352 A | 7/1998 | Swanson et al. |
| 5,797,849 A | 8/1998 | Vesely et al. |
| 5,822,391 A | 10/1998 | Whitting |
| 5,908,415 A | 6/1999 | Sinofsky |
| 5,947,959 A | 9/1999 | Sinofsky |
| 5,956,355 A | 9/1999 | Swanson et al. |
| 5,989,189 A | 11/1999 | LeBlanc et al. |
| 6,111,645 A | 8/2000 | Tearney et al. |
| 6,134,003 A | 10/2000 | Tearney et al. |
| 6,148,095 A | 11/2000 | Prause et al. |
| 6,160,826 A | 12/2000 | Swanson et al. |
| 6,191,862 B1 | 2/2001 | Swanson et al. |
| 6,195,445 B1 | 2/2001 | Jolly et al. |
| 6,208,883 B1 | 3/2001 | Holupka et al. |
| 6,270,492 B1 | 8/2001 | Sinofsky |
| 6,282,011 B1 | 8/2001 | Tearney et al. |
| 6,302,875 B1 | 10/2001 | Makower et al. |
| 6,348,960 B1 | 2/2002 | Etori et al. |
| 6,381,350 B1 | 4/2002 | Klingensmith et al. |
| 6,385,332 B1 | 5/2002 | Zahalka et al. |
| 6,421,164 B2 | 7/2002 | Tearney et al. |
| 6,445,939 B1 | 9/2002 | Swanson et al. |
| 6,471,656 B1 | 10/2002 | Shalman et al. |
| 6,485,413 B1 | 11/2002 | Boppart et al. |
| 6,501,551 B1 | 12/2002 | Tearney et al. |
| 6,552,796 B2 | 4/2003 | Magnin et al. |
| 6,564,087 B1 | 5/2003 | Pitris et al. |
| 6,565,514 B2 | 5/2003 | Svanerudh et al. |
| 6,570,659 B2 | 5/2003 | Schmitt |
| 6,585,660 B2 | 7/2003 | Dorando et al. |
| 6,692,824 B2 | 2/2004 | Benz et al. |
| 6,697,667 B1 | 2/2004 | Lee et al. |
| 6,706,004 B2 | 3/2004 | Tearney et al. |
| 6,716,178 B1 | 4/2004 | Kilpatrick et al. |
| 6,718,089 B2 | 4/2004 | James et al. |
| 6,728,566 B1 | 4/2004 | Subramanyan et al. |
| 6,731,973 B2 | 5/2004 | Voith |
| 6,760,112 B2 | 7/2004 | Reed et al. |
| 6,785,409 B1 | 8/2004 | Suri |
| 6,868,736 B2 | 3/2005 | Sawatari et al. |
| 6,879,851 B2 | 4/2005 | McNamara et al. |
| 6,891,984 B2 | 5/2005 | Petersen et al. |
| 6,932,809 B2 | 8/2005 | Sinofsky |
| 6,937,696 B1 | 8/2005 | Mostafavi |
| 6,942,657 B2 | 9/2005 | Sinofsky et al. |
| 6,947,040 B2 | 9/2005 | Tek et al. |
| 6,973,202 B2 | 12/2005 | Mostafavi |
| 6,974,557 B1 | 12/2005 | Webler et al. |
| 7,068,831 B2 | 6/2006 | Florent et al. |
| 7,134,994 B2 | 11/2006 | Alpert et al. |
| 7,191,100 B2 | 3/2007 | Mostafavi |
| 7,208,333 B2 | 4/2007 | Flanders et al. |
| 7,231,243 B2 | 6/2007 | Tearney et al. |
| 7,241,286 B2 | 7/2007 | Atlas |
| 7,298,478 B2 | 11/2007 | Gilbert et al. |
| 7,301,644 B2 | 11/2007 | Knighton et al. |
| 7,321,677 B2 | 1/2008 | Evron et al. |
| 7,329,223 B1 | 2/2008 | Ainsworth et al. |
| 7,355,699 B2 | 4/2008 | Gilbert et al. |
| 7,359,554 B2 | 4/2008 | Klingensmith et al. |
| 7,397,935 B2 | 7/2008 | Kimmel et al. |
| 7,408,648 B2 | 8/2008 | Kleen et al. |
| 7,412,141 B2 | 8/2008 | Gowda et al. |
| 7,414,779 B2 | 8/2008 | Huber et al. |
| 7,415,049 B2 | 8/2008 | Flanders et al. |
| 7,450,241 B2 | 11/2008 | Zuluaga |
| RE40,608 E | 12/2008 | Glover et al. |
| 7,492,522 B2 | 2/2009 | Gilbert et al. |
| 7,532,920 B1 | 5/2009 | Ainsworth et al. |
| 7,576,861 B2 | 8/2009 | Gilbert et al. |
| 7,593,559 B2 | 9/2009 | Toth et al. |
| 7,610,081 B2 | 10/2009 | Redel |
| 7,619,646 B2 | 11/2009 | Freifeld et al. |
| 7,625,366 B2 | 12/2009 | Atlas |
| 7,627,156 B2 | 12/2009 | Margolis et al. |
| 7,650,179 B2 | 1/2010 | Redel et al. |
| 7,679,754 B2 | 3/2010 | Zuluaga |
| 7,697,972 B2 | 4/2010 | Verard et al. |
| 7,706,585 B2 | 4/2010 | Kleen |
| 7,711,413 B2 | 5/2010 | Feldman et al. |
| 7,729,746 B2 | 6/2010 | Redel et al. |
| 7,733,497 B2 | 6/2010 | Yun et al. |
| 7,742,797 B2 | 6/2010 | Redel et al. |
| 7,783,337 B2 | 8/2010 | Feldman et al. |
| 7,783,338 B2 | 8/2010 | Ainsworth et al. |
| 7,785,286 B2 | 8/2010 | Magnin et al. |
| 7,792,342 B2 | 9/2010 | Barbu et al. |
| 7,801,343 B2 | 9/2010 | Unal et al. |
| 7,813,609 B2 | 10/2010 | Petersen et al. |
| 7,831,078 B2 | 11/2010 | Unal et al. |
| 7,843,976 B2 | 11/2010 | Cable et al. |
| 7,848,791 B2 | 12/2010 | Schmitt et al. |
| 7,853,316 B2 | 12/2010 | Milner et al. |
| 7,869,663 B2 | 1/2011 | Buckland et al. |
| 7,872,759 B2 | 1/2011 | Tearney et al. |
| 7,916,387 B2 | 3/2011 | Schmitt |
| 7,918,793 B2 | 4/2011 | Altmann et al. |
| 7,925,327 B2 | 4/2011 | Weese |
| 7,930,014 B2 | 4/2011 | Huennekens et al. |
| 7,935,060 B2 | 5/2011 | Schmitt et al. |
| 7,967,743 B2 | 6/2011 | Ishihara |
| 7,988,633 B2 | 8/2011 | Hossack et al. |
| 7,991,105 B2 | 8/2011 | Mielekamp et al. |
| 8,029,447 B2 | 10/2011 | Kanz et al. |
| 8,116,605 B2 | 2/2012 | Petersen et al. |
| 8,206,374 B2 | 6/2012 | Duane et al. |
| 8,206,377 B2 | 6/2012 | Petroff |
| 8,208,995 B2 | 6/2012 | Tearney et al. |
| 8,223,143 B2 | 7/2012 | Dastmalchi et al. |
| 8,259,303 B2 | 9/2012 | Johnson et al. |
| 8,290,228 B2 | 10/2012 | Cohen et al. |
| 8,298,147 B2 | 10/2012 | Huennekens et al. |
| 8,315,282 B2 | 11/2012 | Huber et al. |
| 8,325,419 B2 | 12/2012 | Schmitt |
| 8,351,665 B2 | 1/2013 | Tearney et al. |
| 8,358,461 B2 | 1/2013 | Huber et al. |
| 8,423,121 B2 | 4/2013 | Wang et al. |
| 8,449,468 B2 | 5/2013 | Petersen et al. |
| 8,457,375 B2 | 6/2013 | Rieber et al. |
| 8,457,440 B1 | 6/2013 | Johnson |
| 8,463,007 B2 | 6/2013 | Steinberg et al. |
| 8,478,384 B2 | 7/2013 | Schmitt et al. |
| 8,478,387 B2 | 7/2013 | Xu |
| 8,503,844 B2 | 8/2013 | Petersen et al. |
| 8,542,900 B2 | 9/2013 | Tolkowsky et al. |

(56) References Cited

U.S. PATENT DOCUMENTS

| | | | |
|---|---|---|---|
| 8,556,820 B2 | 10/2013 | Alpert et al. | |
| 8,562,537 B2 | 10/2013 | Alpert et al. | |
| 8,571,639 B2 | 10/2013 | Mostafavi | |
| 8,581,643 B1 | 11/2013 | Schmitt | |
| 8,582,109 B1 | 11/2013 | Schmitt | |
| 8,582,619 B2 | 11/2013 | Adler | |
| 8,582,934 B2 | 11/2013 | Adler et al. | |
| 8,670,603 B2 | 3/2014 | Tolkowsky et al. | |
| 8,687,201 B2 | 4/2014 | Adler | |
| 8,693,756 B2 | 4/2014 | Tolkowsky et al. | |
| 8,700,130 B2 | 4/2014 | Iddan et al. | |
| 8,781,193 B2 | 7/2014 | Steinberg et al. | |
| 8,786,336 B1 | 7/2014 | Schmitt | |
| 8,831,321 B1 | 9/2014 | Elbasiony | |
| 8,855,744 B2 | 10/2014 | Tolkowsky et al. | |
| 8,909,323 B2 | 12/2014 | Baumgart | |
| 8,913,084 B2 | 12/2014 | Chen et al. | |
| 8,948,228 B2 | 2/2015 | Adler | |
| 8,953,911 B1 | 2/2015 | Xu et al. | |
| 8,983,580 B2 | 3/2015 | Boppart et al. | |
| 9,069,396 B2 | 6/2015 | Adler et al. | |
| 9,173,591 B2 | 11/2015 | Elbasiony | |
| 9,308,052 B2 | 4/2016 | Tolkowsky et al. | |
| 9,351,698 B2 | 5/2016 | Dascal et al. | |
| 9,404,731 B2 | 8/2016 | Adler et al. | |
| 9,435,956 B1 | 9/2016 | Xu et al. | |
| 9,488,464 B1 | 11/2016 | Schmitt | |
| 9,629,571 B2 | 4/2017 | Tolkowsky et al. | |
| 2002/0115931 A1 | 8/2002 | Strauss et al. | |
| 2002/0161351 A1 | 10/2002 | Samson et al. | |
| 2004/0006277 A1 | 1/2004 | Langenhove et al. | |
| 2005/0043614 A1 | 2/2005 | Huizenga et al. | |
| 2005/0201662 A1 | 9/2005 | Petersen et al. | |
| 2005/0238067 A1 | 10/2005 | Choi | |
| 2005/0249391 A1 | 11/2005 | Kimmel et al. | |
| 2006/0095065 A1 | 5/2006 | Tanimura et al. | |
| 2006/0135870 A1 | 6/2006 | Webler | |
| 2006/0155184 A1* | 7/2006 | Florent | G06T 7/0012 600/407 |
| 2006/0165270 A1 | 7/2006 | Borgert et al. | |
| 2006/0187537 A1 | 8/2006 | Huber et al. | |
| 2006/0203859 A1 | 9/2006 | Cable et al. | |
| 2006/0241465 A1 | 10/2006 | Huennekens et al. | |
| 2006/0241503 A1 | 10/2006 | Schmitt et al. | |
| 2006/0244973 A1 | 11/2006 | Yun et al. | |
| 2007/0024617 A1 | 2/2007 | Poole | |
| 2007/0060822 A1 | 3/2007 | Alpert et al. | |
| 2007/0066890 A1 | 3/2007 | Maschke | |
| 2007/0115481 A1 | 5/2007 | Toth et al. | |
| 2007/0123771 A1 | 5/2007 | Redel et al. | |
| 2007/0135803 A1 | 6/2007 | Belson | |
| 2007/0165916 A1 | 7/2007 | Cloutier et al. | |
| 2007/0167710 A1 | 7/2007 | Unal et al. | |
| 2007/0232933 A1 | 10/2007 | Gille et al. | |
| 2007/0260198 A1 | 11/2007 | Atlas | |
| 2007/0293932 A1 | 12/2007 | Zilla et al. | |
| 2008/0100612 A1 | 5/2008 | Dastmalchi et al. | |
| 2008/0161696 A1 | 7/2008 | Schmitt et al. | |
| 2008/0165366 A1 | 7/2008 | Schmitt et al. | |
| 2008/0221439 A1 | 9/2008 | Iddan et al. | |
| 2008/0221440 A1 | 9/2008 | Iddan et al. | |
| 2008/0221442 A1 | 9/2008 | Tolkowsky et al. | |
| 2008/0228086 A1 | 9/2008 | Ilegbusi et al. | |
| 2008/0281205 A1 | 11/2008 | Naghavi et al. | |
| 2009/0027051 A1 | 1/2009 | Stuber et al. | |
| 2009/0174931 A1 | 7/2009 | Huber et al. | |
| 2009/0204134 A1 | 8/2009 | Kassab | |
| 2009/0306520 A1 | 12/2009 | Schmitt et al. | |
| 2010/0076320 A1 | 3/2010 | Petersen et al. | |
| 2010/0086190 A1* | 4/2010 | Sakaguchi | G06T 15/08 382/132 |
| 2010/0094127 A1* | 4/2010 | Xu | A61B 5/0066 600/425 |
| 2010/0157041 A1 | 6/2010 | Klaiman et al. | |
| 2010/0160764 A1 | 6/2010 | Steinberg et al. | |
| 2010/0160773 A1 | 6/2010 | Cohen et al. | |
| 2010/0161023 A1 | 6/2010 | Cohen et al. | |
| 2010/0172556 A1 | 7/2010 | Cohen et al. | |
| 2010/0191102 A1 | 7/2010 | Steinberg et al. | |
| 2010/0222671 A1 | 9/2010 | Cohen et al. | |
| 2010/0228076 A1 | 9/2010 | Blank et al. | |
| 2010/0253949 A1 | 10/2010 | Adler et al. | |
| 2011/0007315 A1 | 1/2011 | Petersen et al. | |
| 2011/0071404 A1 | 3/2011 | Schmitt et al. | |
| 2011/0071405 A1 | 3/2011 | Judell et al. | |
| 2011/0101207 A1 | 5/2011 | Schmitt | |
| 2011/0151980 A1 | 6/2011 | Petroff | |
| 2011/0157686 A1 | 6/2011 | Huber et al. | |
| 2011/0172511 A1 | 7/2011 | Schmitt et al. | |
| 2011/0178413 A1 | 7/2011 | Schmitt et al. | |
| 2011/0190586 A1 | 8/2011 | Kemp | |
| 2011/0216325 A1 | 9/2011 | Schmitt | |
| 2011/0228280 A1 | 9/2011 | Schmitt et al. | |
| 2011/0230758 A1 | 9/2011 | Eichler | |
| 2011/0257545 A1 | 10/2011 | Suri | |
| 2011/0319752 A1 | 12/2011 | Steinberg et al. | |
| 2012/0004529 A1 | 1/2012 | Tolkowsky et al. | |
| 2012/0029339 A1 | 2/2012 | Cohen et al. | |
| 2012/0057157 A1 | 3/2012 | Petersen et al. | |
| 2012/0075638 A1* | 3/2012 | Rollins | A61B 1/00009 356/479 |
| 2012/0162660 A1 | 6/2012 | Kemp | |
| 2012/0310081 A1 | 6/2012 | Adler et al. | |
| 2012/0224751 A1 | 9/2012 | Kemp et al. | |
| 2012/0236883 A1 | 9/2012 | Adler | |
| 2012/0238869 A1 | 9/2012 | Schmitt et al. | |
| 2012/0250028 A1 | 10/2012 | Schmitt et al. | |
| 2012/0300215 A1 | 11/2012 | Johnson et al. | |
| 2012/0300216 A1 | 11/2012 | Johnson et al. | |
| 2012/0323311 A1* | 12/2012 | McClain | A61L 31/10 623/1.42 |
| 2013/0006105 A1 | 1/2013 | Furuichi | |
| 2013/0010303 A1 | 1/2013 | Petersen et al. | |
| 2013/0012811 A1 | 1/2013 | Schmitt et al. | |
| 2013/0023761 A1 | 1/2013 | Petroff | |
| 2013/0051728 A1 | 2/2013 | Petroff | |
| 2013/0072805 A1 | 3/2013 | Schmitt et al. | |
| 2013/0123616 A1 | 5/2013 | Merritt et al. | |
| 2013/0303910 A1 | 11/2013 | Hubbard et al. | |
| 2013/0310698 A1 | 11/2013 | Judell et al. | |
| 2014/0018669 A1 | 1/2014 | Xu | |
| 2014/0024931 A1 | 1/2014 | Winston et al. | |
| 2014/0094660 A1 | 4/2014 | Tolkowsky et al. | |
| 2014/0094689 A1 | 4/2014 | Cohen et al. | |
| 2014/0094691 A1 | 4/2014 | Steinberg et al. | |
| 2014/0094692 A1 | 4/2014 | Tolkowsky et al. | |
| 2014/0094693 A1 | 4/2014 | Cohen et al. | |
| 2014/0094697 A1 | 4/2014 | Petroff et al. | |
| 2014/0114182 A1 | 4/2014 | Petersen et al. | |
| 2014/0114184 A1 | 4/2014 | Klaiman et al. | |
| 2014/0114185 A1 | 4/2014 | Tolkowsky et al. | |
| 2014/0142427 A1 | 5/2014 | Petroff | |
| 2014/0142432 A1 | 5/2014 | Hutchins et al. | |
| 2014/0142436 A1 | 5/2014 | Hutchins et al. | |
| 2014/0187929 A1 | 7/2014 | Schmitt et al. | |
| 2014/0218742 A1 | 8/2014 | Adler | |
| 2014/0249407 A1 | 9/2014 | Adler et al. | |
| 2014/0257087 A1* | 9/2014 | Elbasiony | A61B 5/061 600/424 |
| 2014/0268167 A1* | 9/2014 | Friedman | G01J 9/02 356/479 |
| 2014/0270445 A1* | 9/2014 | Kemp | A61B 5/6852 382/131 |
| 2014/0276011 A1 | 9/2014 | Schmitt et al. | |
| 2014/0276020 A1 | 9/2014 | Hutchins et al. | |
| 2014/0309536 A1 | 10/2014 | Douk et al. | |
| 2014/0379269 A1 | 12/2014 | Schmitt | |
| 2015/0153157 A1 | 6/2015 | Schmitt et al. | |
| 2015/0119707 A1 | 7/2015 | Schmitt | |
| 2015/0192405 A1 | 7/2015 | Schmitt | |
| 2015/0297373 A1 | 10/2015 | Schmitt et al. | |
| 2015/0370229 A1 | 12/2015 | Adler et al. | |
| 2016/0000406 A1 | 1/2016 | Petroff | |

(56) References Cited

U.S. PATENT DOCUMENTS

| | | | |
|---|---|---|---|
| 2016/0022208 A1* | 1/2016 | Gopinath | A61B 5/02007 |
| | | | 600/427 |
| 2016/0058307 A1 | 3/2016 | Svanerudh | |
| 2016/0070066 A1 | 3/2016 | Schmitt et al. | |
| 2016/0073885 A1 | 3/2016 | Adler | |
| 2016/0174925 A1 | 6/2016 | Dascal et al. | |
| 2016/0213253 A1* | 7/2016 | Wang | A61B 5/0066 |
| 2016/0279303 A1* | 9/2016 | Zhang | A61L 31/10 |
| 2016/0313507 A1 | 10/2016 | Adler et al. | |
| 2016/0335763 A1* | 11/2016 | Ambwani | G06T 7/0012 |
| 2016/0335766 A1* | 11/2016 | Ambwani | A61B 34/20 |
| 2017/0024532 A1* | 1/2017 | Gopinath | A61B 34/10 |
| 2017/0024910 A1* | 1/2017 | Griffin | G06T 11/003 |
| 2019/0096063 A1* | 3/2019 | Ambwani | A61B 5/6852 |

FOREIGN PATENT DOCUMENTS

| | | |
|---|---|---|
| WO | 2006076409 | 7/2006 |
| WO | 2007002685 | 1/2007 |
| WO | 2011038044 | 3/2011 |
| WO | 2012176191 | 12/2012 |
| WO | 2013175472 | 11/2013 |
| WO | 2014002095 | 3/2014 |

OTHER PUBLICATIONS

Kassab et al., "The pattern of coronary arteriolar bifurcations and the uniform shear hypothesis," Annals of Biomedical Engineering 23 (1): 13-20, 1995.

Hariri et al., "An automatic image processing algorithm for initiating and terminating intracoronary OFDI pullback" Biomedical Optics Express 1:2 566-573 (Sep. 1, 2010).

Harrison et al., "The value of lesion cross-sectional area determined by quantitative coronary angiography in assessing the physiologic significance of proximal left anterior descending coronary arterial stenoses," Circulation 69:6 1111-1119, 1984.

Kirkeeide, "Coronary obstructions, morphology, and physiological significance," in Reiber JHC and Serruys PW (eds.), Quantitative Coronary Arteriography, Kluwer Academic Publishers, the Netherlands, 1991, pp. 229-244.

Kolyva et al., "Increased diastolic time fraction as beneficial adjunct of α1-adrenergic receptor blockade after percutaneous coronary intervention," Am J Physiol Heart Circ Physiol 295: H2054-H2060, 2008.

Kolyva et al., "'Windkesselness' of coronary arteries hampers assessment of human coronary wave speed by single-point technique," Am J Physiol Heart Circ Physiol, 295: H482-H490, 2008.

Laslett, "Normal left main coronary artery diameter can be predicted from diameters of its branch vessels," Clinical Cardiology 18 (10): 580-582, 1995.

Ofili et al., "Differential characterization of blood flow, velocity, and vascular resistance between proximal and distal normal epicardial human coronary arteries: analysis by intracoronary Doppler spectral flow velocity," Am Heart J. 130:1 37-46, 1995.

Ohta et al., "Rheological Changes After Stenting of a Cerebral Aneurysm: A Finite Element Modeling Approach," Cardiovascular and Interventional Radiology (2005) 28:768-772.

Pijls et al., "Fractional Flow Reserve (FFR) Post-Stent Registry Investigators" Coronary pressure measurement after stenting predicts adverse events at follow-up: a multicenter registry, Circulation 2002; 105:2950-2954.

Seiler et al., "Basic structure-function relations of the epicardial coronary vascular tree, Basis of quantitative coronary arteriography for diffuse coronary artery disease," Circulation 85 (6): 1987-2003, 1992.

Siebes et al., "Single-wire pressure and flow velocity measurement to quantify coronary stenosis hemodynamics and effects of percutaneous interventions," Circulation 109:756-762, 2004.

Sihan et al., "A Novel Approach to Quantitative Analysis of Intravascular Optical Coherence Tomography Imaging," Computers in Cardiology 2008; 35:1089-1092.

Sihan et al., "Fully Automatic Three-Dimensional Quantitative Analysis of Intracoronary Optical Coherence Tomography: Method and Validation," Catheterization and Cardiovascular Interventions 74:1058-1065 (2009).

Spaan, "Coronary Blood Flow," Ch 12. Dordrecht, The Netherlands: Kluwer Acedemic Publishers, Boston; 1991: pp. 333-361.

Takagi et al., "Clinical potential of intravascular ultrasound for physiological assessment of coronary stenosis," Circulation 100: 250-255,1999.

Verhoeff et al., "Influence of percutaneous coronary intervention on coronary microvascular resistance index," Circulation 111:76-82, 2005.

White et al., "Does visual interpretation of the coronary angiogram predict the physiologic importance of coronary stenoses?," N. Engl J Med 310:13 819-824,1984.

Wilson et al., "Prediction of the physiologic significance of coronary arterial lesions by quantitative lesion geometry in patients with limited coronary artery disease," Circulation 75: 723-732, 1987.

Perez-Rovira et al., "Deformable Registration of Retinal Fluorescein Angiogram Sequences Using Vasculature Structures", 32nd Annual Cont. of IEEE EMBS, 2010, pp. 4383-4386.

Herrington et al., "Semi-automated boundary detection for intravascular ultrasound," Computers in Cardiology 1992 Proceedings., pp. 103-106, Oct. 1992.

Sonka et al., "Segmentation of intravascular ultrasound images: a knowledge-based approach," IEEE Transactions on Medical Imaging, 14(4):719-732, Dec. 1995.

Mojsilovic et al., "Automatic segmentation of intravascular ultrasound images: A texture-based approach," Annals of Biomedical Engineering, 25:1059-1071, Nov. 1997.

Gil et al., "Automatic segmentation of artery wall in coronary IVUS images: a probabilistic approach," Computers in Cardiology 2000; 27:687-690.

Haas et al., "Segmentation of 3D intravascular ultrasonic images based on a random field model," Ultrasound in Medicine & Biology, 26:2, 297-306, 2000.

Kovalski et al., "Three-dimensional automatic quantitative analysis of intravascular ultrasound images," Ultrasound in Medicine & Biology, 26(4):527-537, 2000.

Pujol et al., "Intravascular Ultrasound Images Vessel Characterization using AdaBoost," Functional Imaging and Modeling of the Heart: Lecture Notes in Computer Science, pp. 242-251, 2003.

Taki et al., "Automatic segmentation of calcified plaques and vessel borders in IVUS images," International Journal of Computer Assisted Radiology and Surgery, 3(3-4):347-354, Sep. 2008.

van den Berg et al., "Using three-dimensional rotational angiography for sizing of covered stents," Am. J. Roentgenology, 178:149-152 (2002).

Wong et al., "A novel method of coronary stent sizing using intravascular ultrasound: safety and clinical outcomes," Int. J. Angiol., 18(1): 22-24 2009.

Bonnema et al., "An automatic algorithm for detecting stent endothelialization from volumetric optical coherence tomography datasets", Physics in Medicine and Biology, 53 :12, Jun. 21, 2008, pp. 3083-3098.

Unal et al., "Stent implant follow-up in intravascular optical coherence tomography images," Int J Cardiovasc Imaging, DOI 10.1007/s10554-009-9508-4, published online Sep. 24, 2009, 8 pgs.

Xu et al., "Characterization of atherosclerosis plaques by measuring both backscattering and attenuation coefficients in optical coherence tomography," Journal of Biomedical Optics, 13:3, May/Jun. 2008, 8 pgs.

Takano et al., "Evaluation by Optical Coherence Tomography of Neointimal Coverage of Sirolimus-Eiuting Stent Three Months After Implantation," American Journal of Cardiology, vol. 99, No. 8, Apr. 14, 2007, pp. 1033-1038.

Tung et al., "Automatic Detection of Coronary Stent Struts in Intravascular OCT Imaging," Proceedings of SPIE, vol. 8315, Feb. 22, 2012 (8 pgs.).

(56) References Cited

OTHER PUBLICATIONS

Shengxian Tu et al., "In vivo comparison of arterial lumen dimensions assessed by co-registered three-dimensional (3D) quantitative coronary angiography, intravascular ultrasound and optical coherence tomography", Int. J. Cardiovasc Imaging (2012) 28:1315-1327.

Palti-Wasserman et al., "Identifying and Tracking a Guide Wire in the Coronary Arteries During Angioplasty from X-Ray Images", IEEE transactions on biomedical engineering, 44:2, Feb. 1997, pp. 152-164.

Dave Fornell, "The Advantages and Disadvantages of OCT vs. IVUS", Diagnostic and Interventional Cardiology, May 18, 2011, pp. 1-4.

Wang et al., "Automatic detection of bioresorbable vascular scaffold struts in intravascular optical coherence tomography pullback runs", Biomedical Optics Express, vol. 5, No. 10 (Oct. 2014) pp. 3589-3602.

Bruining et al., "Automated Three-Dimensional Detection of Intracoronary Stent Struts in Optical Coherence Tomography Images", Computing in Cardiology 2011; 38:221-224.

Tsantis et al., "Automatic vessel lumen segmentation and stent strut detection in intravascular optical coherence tomography", Am. Assoc. Phys. Med., Med Phys. 39(1), Jan. 2012, pp. 503-513.

International Search Report and Written Opinion of the International Searching Authority for International Application No. PCT/US2017/032869 mailed from the International Searching Authority dated Jul. 20, 2017 (17 pages).

\* cited by examiner

INTRAVASCULAR ABSORBABLE STENT DETECTION AND DIAGNOSTIC METHODS AND SYSTEMS

CROSS-REFERENCE TO PRIOR APPLICATIONS

This application claims priority to and the benefit of U.S. Provisional Patent Application No. 62/336,931, filed on May 16, 2016, the disclosure of which is herein incorporated by reference in its entirety.

BACKGROUND

Coronary artery disease is one of the leading causes of death worldwide. The ability to better diagnose, monitor, and treat coronary artery diseases can be of life saving importance. Intravascular optical coherence tomography (OCT) is a catheter-based imaging modality that uses light to peer into coronary artery walls and generate images thereof. Utilizing coherent light, interferometry, and micro-optics, OCT can provide video-rate in-vivo tomography within a diseased vessel with micrometer level resolution.

Viewing subsurface structures with high resolution using fiber-optic probes makes OCT especially useful for minimally invasive imaging of internal tissues and organs. OCT allows a clinician to diagnose as well as monitor the progression of coronary artery disease. OCT images provide high-resolution visualization of coronary artery morphology and can be used alone or in combination with other information such as angiography data and other sources of subject data to aid in diagnosis and planning such as stent delivery planning.

A stent is a tube-like structure that often is formed from a mesh. The stent can be inserted into a vessel and expanded to counteract a stenotic condition that constricts blood flow. Stents typically are made of a metal or a polymer scaffold. Stents also can be made of materials that are designed to break down over time under physiologic conditions.

There are several factors that influence the patient outcome when deploying stents. In some procedures, the stent should be expanded to a diameter that corresponds to the diameter of adjacent healthy vessel segments. Stent overexpansion may cause extensive damage to the vessel, making it prone to dissection, disarticulation, and intra-mural hemorrhage. Stent under expansion may inadequately expand the vessel. If the portions of the stent fail to contact the vessel wall, the risk of thrombosis may increase. An underinflated or malapposed stent may fail to restore normal flow. Once a stent is installed, stent malapposition and under expansion of the stent can result in various problems. In addition, bioresorbable stents should be monitored over time to ensure normal stent resorption.

However, bioresorbable stents are challenging to detect relative to metal stents. As a result, there is a need for enhanced strut detection methods for bioresorbable stents.

The present disclosure addresses these challenges and others.

SUMMARY

In part, the disclosure relates to a method of detecting a bioresorbable scaffold in a blood vessel. The method may include storing, in an electronic memory storage device, intravascular image data from a pullback of an intravascular probe through the blood vessel and a bioabsorbable scaffold disposed in the blood vessel, the bioresorbable scaffold having one or more struts. The method may also include generating a plurality of image frames from the stored intravascular image data, the stored intravascular image data includes a plurality of scan lines. The method may also include generating a mask for one or more image frames of the plurality of image frames. The method may also include inverting the mask to generate an inverted mask, wherein the inverted mask includes bright pixel regions separated by dark pixel regions. The method may also include detecting a group of bright pixel regions. The method may also include identifying the group of bright pixel regions as defining a candidate inner region of a strut of the bioresorbable scaffold. Other embodiments of this aspect of the disclosure includes corresponding computer systems, apparatus, and computer programs recorded on one or more computer storage devices, each configured to perform the actions of the methods.

Implementations may include one or more of the following features. The method wherein groupings of the bright pixel regions define a plurality of insular regions separated by a plurality of the dark pixel regions. The method wherein the dark pixel regions correspond to background and bright pixel regions correspond to foreground. In one embodiment, the bright pixel regions correspond to signal and the dark pixel regions correspond to a lack of signal. Signal containing regions are operated upon to detect struts and/or other BRS components. The method wherein identifying a group of the bright pixel regions includes performing multiresolution filtering using a first filter and a second filter, wherein the first filter and the second filter are morphological filters. The method may further include detecting a plurality of zero crossing regions in an image frame or in the inverted mask and excluding one or more candidate inner regions if zero crossing regions are not disposed on two or more sides of a candidate inner region of a strut. The method wherein detecting a group of bright pixel regions is performed on a shape-independent basis, such that boxes or edges are not used to identify the group of bright pixel regions.

The method may further include validating a plurality of detected struts and displaying the validated struts relative to a graphic user interface of an intravascular imaging system. The method may further include determining a strut end face boundary and determining a lumen boundary of the blood vessel. The method may further include determining a separation distance d using a detected lumen boundary and the strut end face boundary. The method may further include detecting a guidewire shadow, detecting a lumen boundary, and detecting a side branch shadow. The method may further include scanning on a per pixel basis and comparing each pixel relative to the local neighborhood thereof to determine if a given pixel is a local intensity maxima. The method may also include measuring a size attribute of at least one strut at a first point in time.

The method may also include measuring a size attribute of the at least one strut at a second point in time. The method may also include calculating a change in the size attribute between the first time and the second time. The method wherein the image is an optical coherence tomography image generated from a plurality of scan lines. The method may further include filtering, using a Laplacian of a Gaussian filter, the inverted image mask to identify one or more interior strut regions. The method wherein one or more of the step of generating a mask; the step of inverting the mask; and the step of detecting a group of bright pixel region are performed by an image processing module of an intravascular data collection system in electronic communication with the electronic memory storage device.

The method may further include filtering the inverted image to identify local intensity maxima in one or more interior strut regions, wherein clusters of local intensity maxima correspond to the location of individual struts in the image. The method may further include combining a location of the one or more interior strut regions of the insular group with a location of local intensity maxima clusters. The method may further include performing a zero crossing analysis to eliminate luminous interior strut regions that are not bounded by a zero crossing detection on all sides. The method may further include generating the image using in vivo measurements obtained using an intravascular imaging probe. The method wherein one or more of the step of converting an image; the step of inverting the image mask; and the step of detecting a group of detecting an insular group of bright pixels are performed by an image processing module of an intravascular data collection system.

The method may further include displaying the validated struts relative to a graphic user interface of an intravascular imaging system. The system may further include instructions to cause the computing device to determine a strut end face boundary. The system may further include instructions to cause the computing device to determine a stent or scaffold separation distance d using a detected lumen boundary and the strut end face boundary. The system may further include instructions to cause the computing device to display the separation distance d on a graphical user interface of an imaging system. Implementations of the described techniques may include hardware, a method or process, or computer software on a computer-accessible medium.

One general aspect includes a method of detecting a bioresorbable device in a blood vessel, the method includes converting an image of a blood vessel to an image mask, the image includes struts of a bioresorbable scaffold; inverting the image mask to create an inverted image mask, detecting an insular group of bright pixels; and filtering the insular group of bright pixels using one or more morphological filters to identify candidate struts; and validating the candidate struts to identify one or more struts of the bioresorbable scaffold. Other embodiments of this aspect include corresponding computer systems, apparatus, and computer programs recorded on one or more computer storage devices, each configured to perform the actions of the methods.

Implementations may include one or more of the following features. The method may further include filtering the inverted image to identify local intensity maxima in one or more interior strut regions, wherein clusters of local intensity maxima correspond to the location of individual struts in the image. The method may further include combining a location of the one or more interior strut regions of the insular group with a location of local intensity maxima clusters. The method may further include performing a zero crossing analysis to eliminate luminous interior strut regions that are not bounded by a zero crossing detection on all sides. The method may further include generating the image using in vivo measurements obtained using an intravascular imaging probe. The method wherein one or more of the step of converting an image; the step of inverting the image mask; and the step of detecting a group of detecting an insular group of bright pixels are performed by an image processing module of an intravascular data collection system.

The method may further include displaying the validated struts relative to a graphic user interface of an intravascular imaging system. The system may further include instructions to cause the computing device to determine a strut end face boundary. The system may further include instructions to cause the computing device to determine a stent or scaffold separation distance d using a detected lumen boundary and the strut end face boundary. The system may further include instructions to cause the computing device to display the separation distance d on a graphical user interface of an imaging system. Implementations of the described techniques may include hardware, a method or process, or computer software on a computer-accessible medium.

One general aspect includes a system for detecting a bioresorbable device having struts in a blood vessel, the system includes one or more memory devices; and a computing device in communication with the memory device, wherein the memory device includes instructions executable by the computing device to cause the computing device to generate a plurality of image frames from intravascular image data stored in the memory device; generate a binary mask for the plurality of image frames. The system also includes instructions to identify inner regions of a first intensity level in each binary mask; identify border regions of a second intensity level in each binary mask, identify one more candidate struts based on a per frame basis based on the relative position of one inner region relative to one or more border regions, and filter candidate struts to exclude candidates if zero crossing regions are not disposed on two or more sides of a candidate strut. Other embodiments of this aspect include corresponding computer systems, apparatus, and computer programs recorded on one or more computer storage devices, each configured to perform the actions of the methods.

Implementations may include one or more of the following features. The system may further include instructions to cause the computing device to determining a strut end face boundary. The system may further include instructions to cause the computing device to determine a stent or scaffold separation distance d using a detected lumen boundary and the strut end face boundary. The system may further include instructions to cause the computing device to display the separation distance d on a graphical user interface of an imaging system. Implementations of the described techniques may include hardware, a method or process, or computer software on a computer-accessible medium.

One general aspect of the disclosure may include storing intravascular image data from a pullback of an intravascular probe through the blood vessel and a bioresorbable stent or scaffold disposed in the blood vessel, the stent or scaffold having one or more struts. The method also may include generating a plurality of image frames from the stored intravascular image data. The method also may include generating a binary mask for the plurality of image frames. The method also may include identifying inner regions of a first intensity level in each binary mask. The method also may include identifying border regions of a second intensity level in each binary mask. The method also may include identifying one more candidate struts on a per frame basis based on relative position of one inner region relative to one or more border regions. Other embodiments of this aspect include corresponding computer systems, apparatus, and computer programs recorded on one or more computer storage devices, each configured to perform the actions of the methods.

Implementations may include one or more of the following features. The method may further include transmitting light through from the intravascular probe through the bioresorbable stent or scaffold. In one embodiment, the light is not transmitted through the bioresorbable stent or scaffold. In one embodiment, the method may include directing light from the intravascular probe to interact with the bioresorbable stent or scaffold. The method may further include receiving, with the intravascular probe, light returned from interior of the bioresorbable stent or scaffold. The method may further include filtering candidate struts to exclude candidates if zero crossing regions are not disposed on two or more sides of a candidate strut. The method may further include displaying validated struts. The method may further include determining a strut end face boundary. The method may further include determining a stent or scaffold separation distance d using a detected lumen boundary and the strut end face boundary. The system may further include instructions to cause the computing device to determining a strut end face boundary.

The system may further include instructions to cause the computing device to determine a stent or scaffold separation distance d using a detected lumen boundary and the strut end face boundary. The system may further include instructions to cause the computing device to display the separation distance d on a graphical user interface of an imaging system. The method may further include the steps of inverting the image to generate an inverted image; and filtering the inverted image to identify local intensity maxima in the luminous interior strut regions, where clusters of local intensity maxima correspond to the location of individual struts in the image. The method may further include the step of combining a location of the luminous interior strut regions with a location of local intensity maxima clusters.

In one embodiment, the method may further include the step of performing a zero crossing analysis to eliminate luminous interior strut regions that are not bounded by a zero crossing on all sides. The method wherein a Laplacian of Gaussian filter is used to filter the inverted image mask to identify the luminous interior strut regions. The method may further include the step of scanning on a per pixel basis and comparing each pixel relative to its local neighborhood to determine if a given pixel is a local intensity maxima. The method including the steps of measuring a size attribute of at least one strut at a first point in time; measuring a size attribute of the same at least one strut at a second point in time; and calculating a change in the size attribute between the first time and the second time. The method may further include generating the image using in vivo measurements obtained using an intravascular imaging probe. The method wherein the image is optical coherence tomography image generated from a plurality of scan lines. Implementations of the described techniques may include hardware, a method or process, or computer software on a computer-accessible medium.

One general aspect may include a processor-based system for detecting struts, the system including one or more memory devices; and a computing device in communication with the memory device, wherein the memory device may include instructions executable by the computing device to cause the computing device to generate a plurality of image frames from intravascular image data stored in the memory device. The processor-based system also may include instructions to generate a binary mask for the plurality of image frames; identify inner regions of a first intensity level in each binary mask. The processor-based system also may include instructions to identify border regions of a second intensity level in each binary mask. The processor-based system also may include instructions to identify one more candidate struts based on a per frame basis based on the relative position of one inner region relative to one or more border regions. The processor-based system also may include instructions to filter candidate struts to exclude candidates if zero crossing regions are not disposed on two or more sides of a candidate strut. Other embodiments of this aspect include corresponding computer systems, apparatus, and computer programs recorded on one or more computer storage devices, each configured to perform the actions of the methods.

Implementations may include one or more of the following features. The system may further include instructions to cause the computing device to determining a strut end face boundary. The system may further include instructions to cause the computing device to determine a stent or scaffold separation distance d using a detected lumen boundary and the strut end face boundary. The system may further include instructions to cause the computing device to display the separation distance d on a graphical user interface of an imaging system. The method may further include the inverting the image to generate an inverted image; and filtering the inverted image to identify local intensity maxima in the luminous interior strut regions, wherein clusters of local intensity maxima correspond to the location of individual struts in the image.

In one embodiment, the method may further include the step of combining a location of the luminous interior strut regions with a location of local intensity maxima clusters. The method may further include the step of performing a zero crossing analysis to eliminate luminous interior strut regions that are not bounded by a zero crossing on all sides. In one embodiment, a Laplacian of Gaussian filter is used to filter the inverted image mask to identify the luminous interior strut regions. The method may further include scanning on a per pixel basis and comparing each pixel relative to its local neighborhood to determine if a given pixel is a local intensity maxima. The method may include measuring a size attribute of at least one strut at a first point in time; measuring a size attribute of the same at least one strut at a second point in time; and calculating a change in the size attribute between the first time and the second time. The method may further include generating the image using in vivo measurements obtained using an intravascular imaging probe. The method wherein the image is optical coherence tomography image generated from a plurality of scan lines. Implementations of the described techniques may include hardware, a method or process, or computer software on a computer-accessible medium.

One general aspect may include a method of detecting struts including converting an image of a blood vessel that may include a scaffold into an image mask, the image including a bioresorbable stent or scaffold having struts, the struts having an image cross section defined by an interior strut region surrounded by a zero crossing luminous strut border; inverting the image mask to create an inverted image mask, the struts having an inverted image mask cross section defined by a luminous strut interior region surrounded by a zero crossing border; and filtering the inverted image mask to identify the luminous interior strut regions, the luminous strut interior regions corresponding to a location of individual struts in the image. Other embodiments of this aspect include corresponding computer systems, apparatus, and computer programs recorded on one or more computer storage devices, each configured to perform the actions of the methods.

Implementations may include one or more of the following features. The method may further include inverting the image to generate an inverted image; and filtering the inverted image to identify local intensity maxima in the luminous interior strut regions, wherein clusters of local intensity maxima correspond to the location of individual struts in the image. The method may further include the step of combining a location of the luminous interior strut regions with a location of local intensity maxima clusters. The method may further include the step of performing a zero crossing analysis to eliminate luminous interior strut regions that are not bounded by a zero crossing on all sides. The method wherein a Laplacian of Gaussian filter is used to filter the inverted image mask to identify the luminous interior strut regions. The method may further include the step of scanning on a per pixel basis and comparing each pixel relative to its local neighborhood to determine if a given pixel is a local intensity maxima.

In one embodiment, the method including the steps of measuring a size attribute of at least one strut at a first point in time; measuring a size attribute of the same at least one strut at a second point in time; and calculating a change in the size attribute between the first time and the second time. The method may further include generating the image using in vivo measurements obtained using an intravascular imaging probe. The method wherein the image is optical coherence tomography image generated from a plurality of scan lines. Implementations of the described techniques may include hardware, a method or process, or computer software on a computer-accessible medium.

A system of one or more computing devices can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

Although, the invention relates to different aspects and embodiments, it is understood that the different aspects and embodiments disclosed herein can be integrated together as a whole or in part, as appropriate. Thus, each embodiment disclosed herein can be incorporated in each of the aspects to varying degrees as appropriate for a given implementation and steps from various methods can be combined without limitation. Notwithstanding the foregoing and the other disclosure herein, embodiments disclosed herein may also be applied in the context of other intravascular imaging systems methods as applicable.

Other features and advantages of the disclosed embodiments will be apparent from the following description and accompanying drawings.

BRIEF DESCRIPTION OF DRAWINGS

The figures are not necessarily to scale, emphasis instead generally being placed upon illustrative principles. The figures are to be considered illustrative in all aspects and are not intended to limit the disclosure, the scope of which is defined only by the claims.

DETAILED DESCRIPTION

Figure 1A:
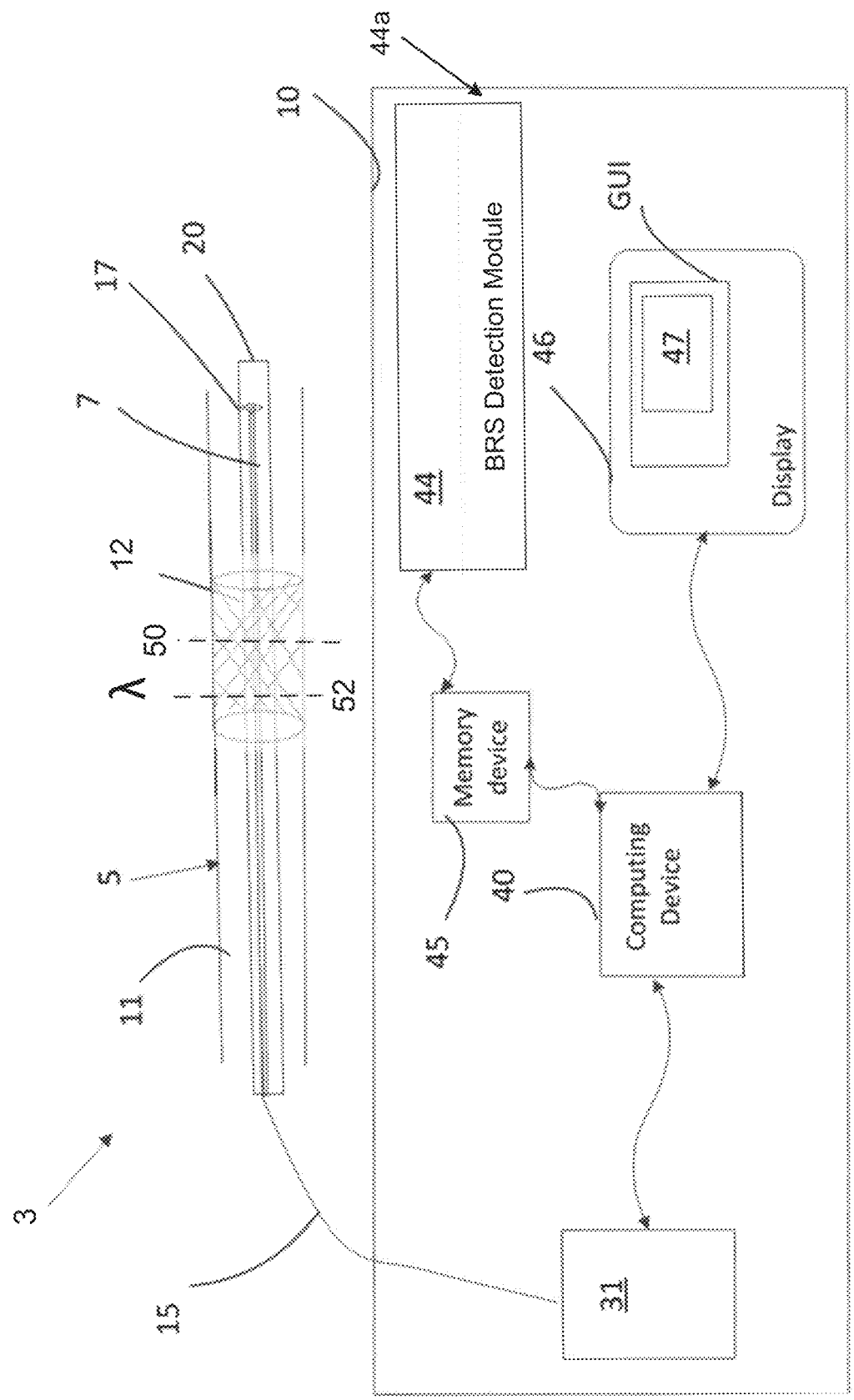
FIG. 1A is an exemplary intravascular data collection system and an associated intravascular data collection probe and related image processing, detection, and other software components according to an illustrative embodiment of the disclosure.

The disclosure provides, in part, methods and systems to detect stents and their component portion or regions such as struts. In particular, the disclosure relates to systems and methods to detect classes or categories of stents and struts that are difficult to detect using intravascular ultrasound and/or angiography such as polymer-based stents/scaffolds, non-metal stents/scaffolds or other implantable devices that are optically detectable. The disclosure also relates to diagnostic methods and systems to detect and measure stents that become difficult to detect over time as result of structural changes therein such as dissolving or absorption of structural material. In some embodiments, the methods described herein are suitable for use with intravascular imaging using light such as interferometric imaging with OCT being an example and other imaging modalities.

In part, the disclosure relates to detecting of radially expandable endoprosthesis, which are adapted to be implanted in a bodily lumen. An "endoprosthesis" corresponds to an artificial device that is placed inside the body. A "lumen" refers to a cavity of a tubular organ such as a blood vessel. A stent or scaffold are examples of such an endoprosthesis. These devices typically contain multiple struts. A stent or scaffold are generally cylindrically shaped devices, which function to hold open and sometimes expand a segment of a blood vessel or other anatomical lumen such as urinary tracts and bile ducts. Such devices are often used in the treatment of atherosclerotic stenosis in blood vessels.

In general, various endoprosthesis include scaffolding that includes a pattern or network of interconnecting structural elements or struts. The scaffolding can be formed from wires, tubes, or sheets of material rolled into a cylindrical shape. In addition, a medicated endoprosthesis may be fabricated by coating the surface of either a metallic or polymeric scaffolding with a polymeric carrier. The polymeric scaffolding may also serve as a carrier of an active agent or drug.

In general, the disclosure relates to the detection, analysis, and/or display of various endoprosthesis. In one embodiment, light that is transmitted into and backscattered from a strut is received by an intravascular data collection system such as an OCT system. This implementation is suitable for use with struts that do not attenuate the light or are partially attenuating or at least able to partially transmit light through the strut/scaffold portion or region. The received light is changed or modulated in intensity because of passing through the strut. The system operates upon datasets that include intensity measurements of the transmitted light and changes thereto. This type of implementation can avoid relying upon shadows for scaffold/strut detection. That is, methods for shadowless or shadow independent strut detection are one embodiment of the disclosure.

Exemplary endoprosthesis such as stents, scaffolds, struts and components and combinations thereof that are made of metal and non-metallic materials, such as polymers or other compounds, that are absorbed by the body or otherwise dissolve or change structurally after being deployed for a period of time in the lumen of an artery such as various absorbable stents, bioresorbable stents or scaffolds, chemical, drug, or medicament eluting stents are suitable for intravascular imaging and data collection using the methods and systems described herein. Optical coherence tomography and other optical imaging methods are amenable to detecting, imaging, and analyzing various endoprosthesis such as bioresorbable stent or scaffolds (BRS), bare-metal stents (BMS), drug-eluting stents (DES), bioresorbable vascular scaffold (BVS) and other stents, struts, and scaffolds suitable for deployment in a blood vessel. In general, bioresorbable or bioabsorbable intravascular devices can be used to refer to the same device, unless otherwise specified.

As used herein endoprosthesis such as BRS, DES, BVS and others can include non-metal stents or metal stents that include non-metal components, the stents and scaffolds described herein and generally used in blood vessels, and components of the foregoing. For example, the components can include struts or other portions or regions of a given BRS. In various examples reference is made to detection of components of a BRS, in general when BRS is referenced, the example is meant to include any suitable endoprosthesis that includes a bioresorbable component such as a strut, scaffold, layer, component, feature, coating, etc.

In one embodiment, various bioresorbable endoprosthesis such as BRS appear as a hollow or bordered box shaped structure in OCT images, with the interior of the box appearing darker and the border of the box appears brighter. The thickness of the border can correlate with the thickness of the outer layer of the BRS. The thickness of the border can correlate with the thickness of a given BRS in one embodiment. The computerized systems and methods disclosed herein use various filtering and image processing steps to scan or operate upon intravascular data such as OCT images to detect this characteristic box or island profile or to enhance its detection such as through one or mask applications or inversion operations. In one embodiment, rather than consider a shape-based approach, an inversion process is used to turn the inner region of a candidate strut into signal containing foreground and then performing image processing relative thereto. In this way, the scaffold is treated as background or not signal containing and a bright set of pixels identified in the interior region of a BRS is used to perform detection.

These steps and others described herein can be used to identify the location of BRS struts in a stented vessel. In turn, the detected struts can be displayed and measured. In one embodiment, the detection is automatic. Once detected, the struts can be integrated with other image information for display to a clinician on a graphical user interface. For example, detected BRS can be overlaid or integrated into various scan line, L-Mode, cross sectional, and/or three-dimensional images of a stented vessel. Various data collection systems and probes can be used to detect BRS.

FIG. 1A is a high level schematic diagram 3 depicting a blood vessel 5, such as an artery, a data collection probe 7 and an intravascular data collection and processing system 10. The system 10 can include for example, an OCT, intravascular ultrasound (IVUS), or other intravascular imaging system. A BRS 12 is shown in the blood vessel 5. The BRS includes a plurality of detectable struts or regions 30.

The system 10 can include various software modules 44 suitable for performing lumen boundary, tissue boundary, BRS detection, BRS evaluation over time, absorption level evaluation for BRS using image data comparisons, and processing, error correction, model comparisons, lumen detection, guide wire detection, mask generation, mask inversion, and various other processes as described herein. The system 10 can include a suitable light source that satisfies the coherence and bandwidth requirements of the applications and data collection described herein. The system 10 can include an ultrasound imaging system. The probe 7 can include a catheter 20 having a catheter portion having one or more optical fibers 15 and a probe tip 17 disposed therein. The probe tip 17 includes a beam director in one embodiment.

As shown, the catheter 20 is introduced into the lumen 11 such as an arterial lumen. The probe 7 can include a rotating or slidable fiber 15 that directs light forward into the lumen 11 or at a direction perpendicular to the longitudinal axis of the fiber 15. As a result, in the case of light that is directed from the side of the probe as the fiber 15 rotates, image data is collected with respect to the walls of the blood vessel 5. The walls of the blood vessel 5 define a lumen boundary. Struts 30 are adjacent to, contact, or enter the wall 5 in some embodiments. This lumen boundary can be detected using the distance measurements obtained from the optical signals collected at the probe tip 17 using lumen detection software component. Edges of struts 30 can be used relative to lumen boundary to measure correct positions of a given BRS. BRS and other features can be identified in the scan lines generated during a pullback through the artery by the probe and within two-dimensional images such as frames of intravascular data.

The probe 7 can include other imaging modalities in addition to OCT such as ultrasound in one embodiment. In one embodiment, the lumen/lumen boundary refers to a portion of the vessel that is first impinged upon when light or ultrasound exists an intravascular imaging probe that generates a signal of interest for imaging the vessel. This excludes any blood flowing in the vessel which is typically removed using image processing in the form of masking. In one embodiment, the lumen or lumen boundary refers to a region of tissue that is disposed in front of the vessel wall and facing the blood containing region of the vessel. The light reaching the lumen boundary can typically pass through a portion of a given BRS.

Figure 1B:
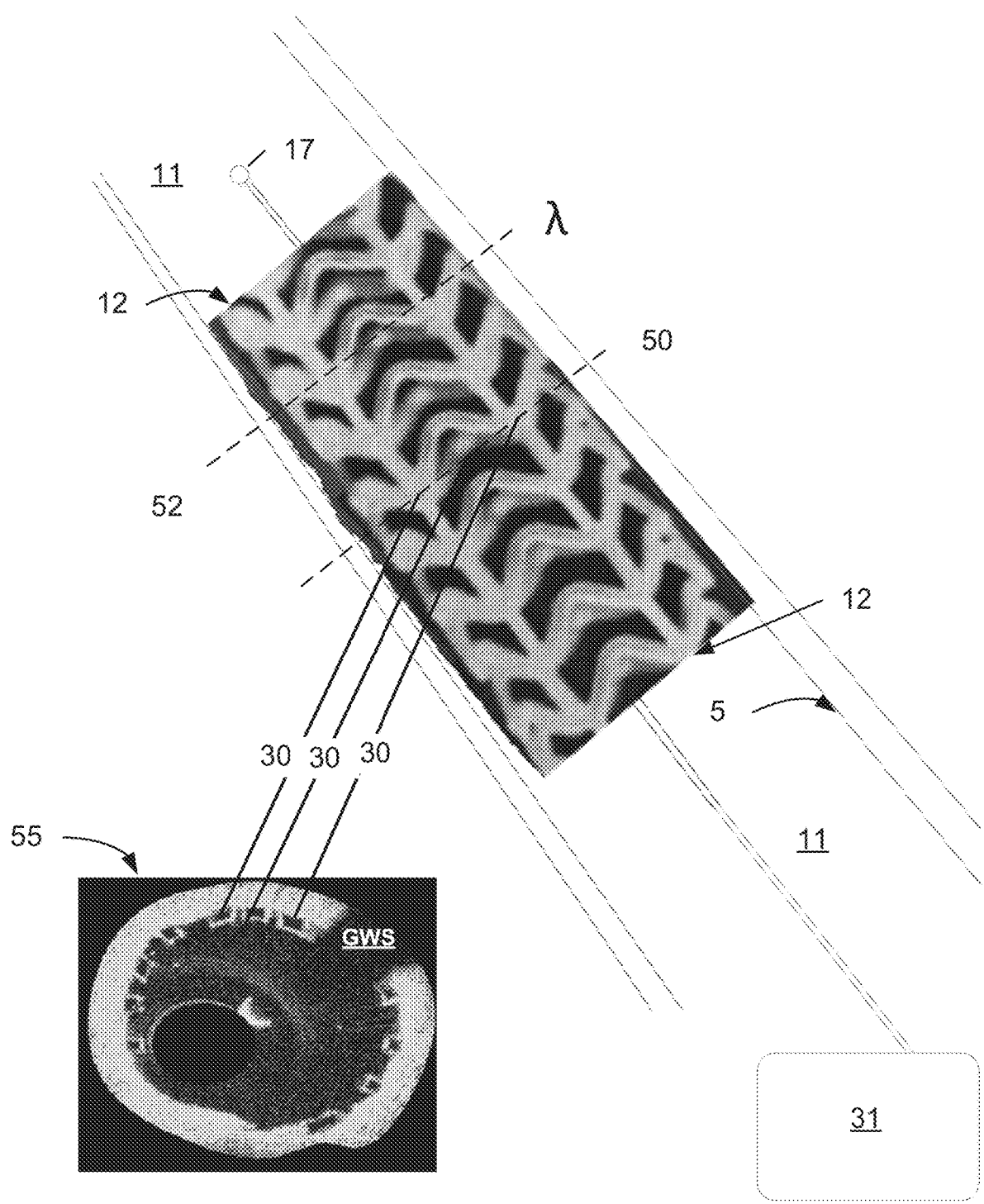
FIG. 1B is a schematic diagram of a BRS being optically imaged with light passing through a portion of the BRS according to an illustrative embodiment of the disclosure.

As shown in FIG. 1A, the probe tip 17 is positioned in the lumen 11 such that it is distal to a stented region of the blood vessel 5. The probe tip 17 is configured to transmit light and receive backscattered light from objects, such as for example BRS 12, and the wall of the blood vessel 5. Various strut portions are disposed in an exemplary cross-section 50 of the BRS 12. As shown in FIGS. 1A and 1B, along an exemplary cross-section 52 of BRS, light from probe tip 17 transmits light $\lambda$ that impinges upon and enters a strut or other BRS component.

Without being held to a particular theory or mechanism, light from within the BRS, from edges of the BRS, and from the wall 5 of the vessel adjacent the BRS returns to the probe tip 17 in response to the incident imaging light. The probe tip 17 and the rest of the data collection probe 7 are pulled through the lumen 11. The probe 7 is in optical communication with an OCT system 10. The OCT system or subsystem 10 that connects to probe 17 via an optical fiber 15 can include a light source such as a laser, an interferometer having a sample arm and a reference arm, various optical paths, a clock generator, photodiodes, and other OCT system components.

In one embodiment, an interface system 31 is coupled to the probe and can receive light exiting the probe 7. In one embodiment, interface system 31 includes a balanced photodiode based system. The interface 31 can include a rotatable coupler to connect to an imaging probe. A computing device 40 such as a computer, processor, ASIC or other device can be part of the OCT system 10 or can be included as a separate subsystem in electrical or optical communication with the OCT system 10. The computing device 40 can include memory, storage, buses and other components suitable for processing data and software 44 such as image data processing stages such as a BRS detection module 44a.

The computing device 40 may include one or more apparatus, devices, and machines for processing data, signals and information, including by way of example a programmable processor, a computer, one or more circuits, or multiple processors or computers or other computing devices. The computing device, in addition to hardware, code that creates an execution environment for the computer program in question, e.g., code that constitutes processor firmware, a stack, a data management system, an operating system, one or more user interface systems, or a combination of one or more of them.

The software modules can include intravascular data detection, analysis, and transformation methods to operate upon scan lines and/or frames of intravascular data to perform one or more of side branch detection, strut candidate selection or identification, candidate strut correlations and comparisons of BRS changes over time, and pullback data collection as discussed below. In one embodiment, the software module 44 compensates for a lack of shadows or a reduced level of shadows generated by one or more portions of a BRS using masking, inversion and filtering processes. In one embodiment, the software module includes an image processing module of an intravascular data collection system in electronic communication with the electronic memory storage device. The image processing modules includes one or more filters, mask inverters, masking operators, intensity detectors, and other image processing operators as described herein.

In one embodiment, two software-based methods or algorithms are used that either run in parallel or sequentially that would identify the BRS struts and the metallic struts independently. The metallic stent detection software module identifies one or more regions or zones along the blood vessel images data that have metallic struts. In these zones or regions, metallic strut detection is performed. Similarly, the BRS detection method identifies the BRS zone or region and then additional techniques as described herein are implemented to perform BRS detection as disclosed herein. These two detection methods can be in parallel or sequential as they are independent processes in one embodiment. Alternatively, an end user may choose to run a BRS detection method only or a metallic stent detection algorithm only. This follows because the end user will typically know what type of stent is deployed (either previously or in the current cath lab workflow).

During some instances, there can be situations when the deployment of a BRS strut failed or a BRS stent was fractured. Hence an end user can use the diagnostic tools disclosed herein to help decide or plan how and where to place a metallic stent on top of the BRS. Alternatively, the end user may choose to stent one lesion with BRS and another with a metallic stent. Thus, in some embodiments, both methods run together to detect metallic stents and BRS.

In one embodiment, the computing device 40 includes or accesses software modules or programs 44, such as a side branch detection module, a lumen detection module, a BRS detection module 44a, a BRS validation module and other software modules. The software modules or programs 44 can include an image data processing pipeline or component modules thereof and one or more graphical user interfaces (GUI). The modules can be subsets of each other and arranged and connected through various inputs, outputs, and data classes.

Figure 7A:
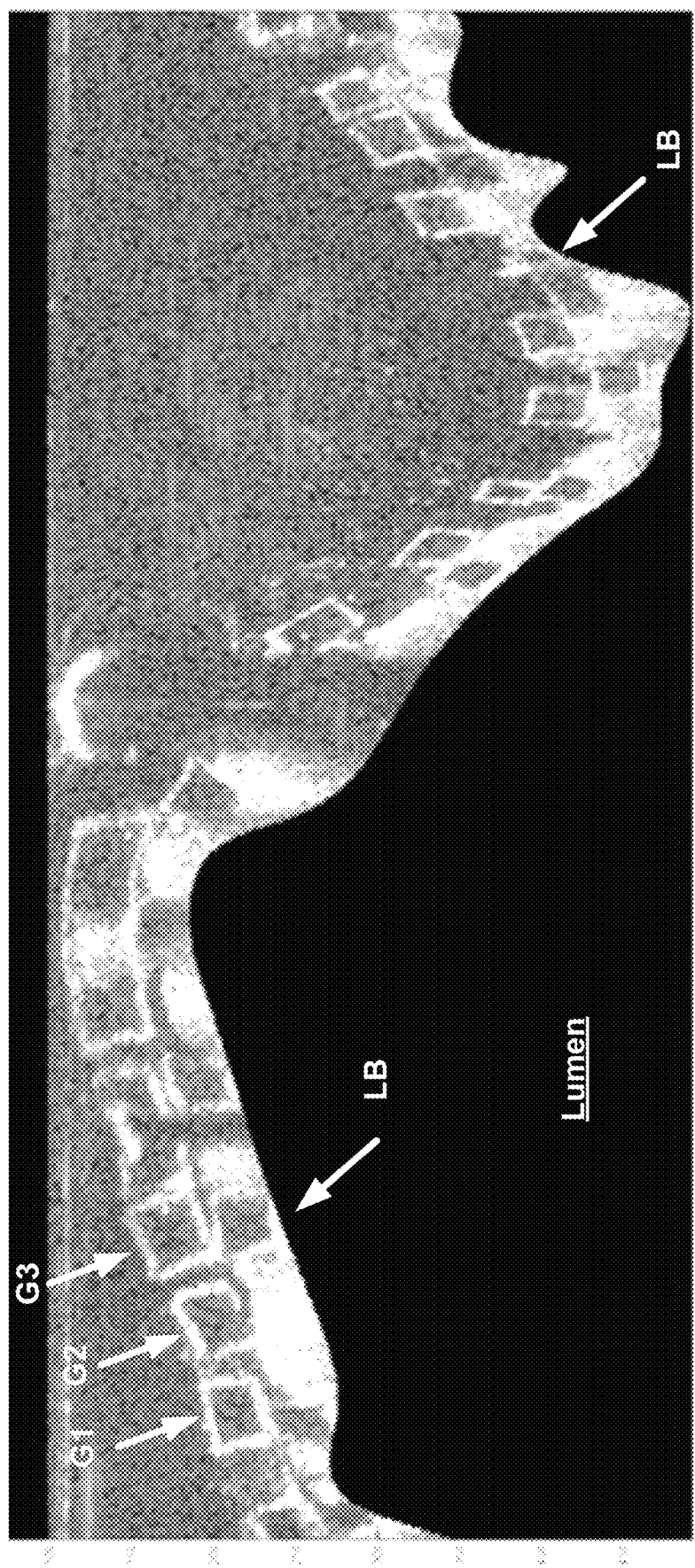
FIG. 7A is a scan line OCT image of a vessel that includes a BRS having struts with local intensity maxima marked according to an illustrative embodiment of the disclosure.
Figure 7B:
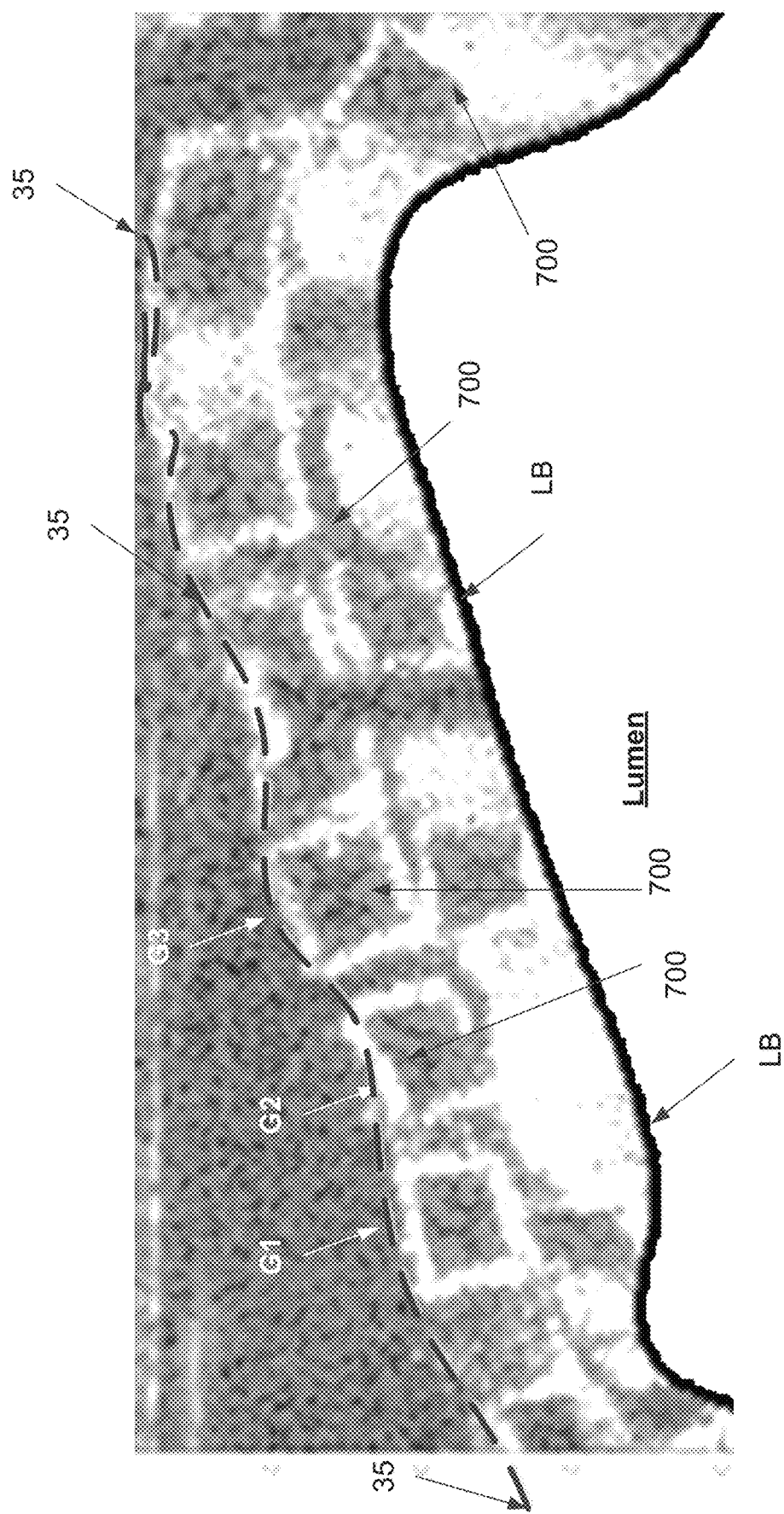
FIG. 7B is a zoomed in view of a portion of FIG. 7A with the dark lumen region removed for clarity and additional features emphasized according to an illustrative embodiment of the disclosure.

An exemplary image processing pipeline and components thereof can constitute one or more software programs or modules 44. The software modules 44 may comprise several image processing algorithms tailored to detect the vessel lumen, side-branches, guide-wires, guide-catheters, BRS and BRS regions. This disclosure relates to image and signal processing and transformation relative to intravascular data to detect a BRS and determine its location and relative position such as to a lumen or tissue border. The boundary 35 of strut end faces for a given BRS can also be detected and displayed in one embodiment such as shown in FIG. 7B. The image data processing pipeline, its components software modules and related methods and any of the methods described herein are stored in memory and executed using one or more computing devices such as a processor.

As shown, in FIG. 1A, a display 46 can also be part of the system 10 for showing information 47 such as cross-sectional and longitudinal views of a blood vessel generated from intravascular data such interferometric or tomographic data or other distance measurement-based data and BRS struts 30 and boundary 35. The image processing software algorithms 44 provide data corresponding to detected image features such as BRS and components or subsets thereof, side-branches, guide-wire etc. and this data is input to the GUI where these features are displayed in a desired format on cross-sectional, longitudinal, and/or 3D display sections of the GUI. The image 55 of FIG. 1B is an example of display information 47 that can be displayed and interacted with using a GUI and various input devices. Specifically, it shows a 2D cross-sectional view of a coronary artery containing a BRS.

In addition, display information 47 can include, without limitation, cross-sectional scan data, longitudinal scans, diameter graphs, image masks, stents, areas of malapposition, lumen border, strut and tissue borders and other images or representations of a blood vessel or the underlying distance measurements obtained using an OCT system and data collection probe. The computing device 40 can also include software or programs 44, which can be stored in one or more memory devices 45, configured to identify struts, absorption levels, and malapposition levels (such as based on a threshold and measured distance comparison), and other blood vessel features which can be displayed and identified such as with text, arrows, color coding, highlighting, contour lines, or other suitable human or machine readable indicia on a computer-based graphic user interface. These displays can be used in cath labs to enhance a given diagnostic procedure or planning procedure. The computing device 40 can also include software or programs 44, 44a, and other operators described herein that can perform one or more method steps such as image processing filtering and detection and inversion.

FIG. 1B is a schematic representation of blood vessel with a BRS 12 disposed therein, in accordance with the present disclosure. Various strut portions are disposed in an exemplary cross-section 50 of the BRS 12. Struts or portions 30 of the BRS are shown as disposed in the frame of intravascular image data 55. The image data or frame 55 is a cross-sectional view of a vessel imaged using OCT. The shadow from the guidewire used to position the OCT probe is identified in this figure and generally in the figures as GWS (guide wire shadow). In general, although used with regard to different figures, struts or portions of BRS are labelled 30 in the figures. The strut portions 30 of the BRS are shown in both the schematic representation of the BRS 12 and the frame of image data 55. The frame of image data is generated using one or more of the system embodiments described herein.

Automatic BRS Detection and Display

Figure 1C:
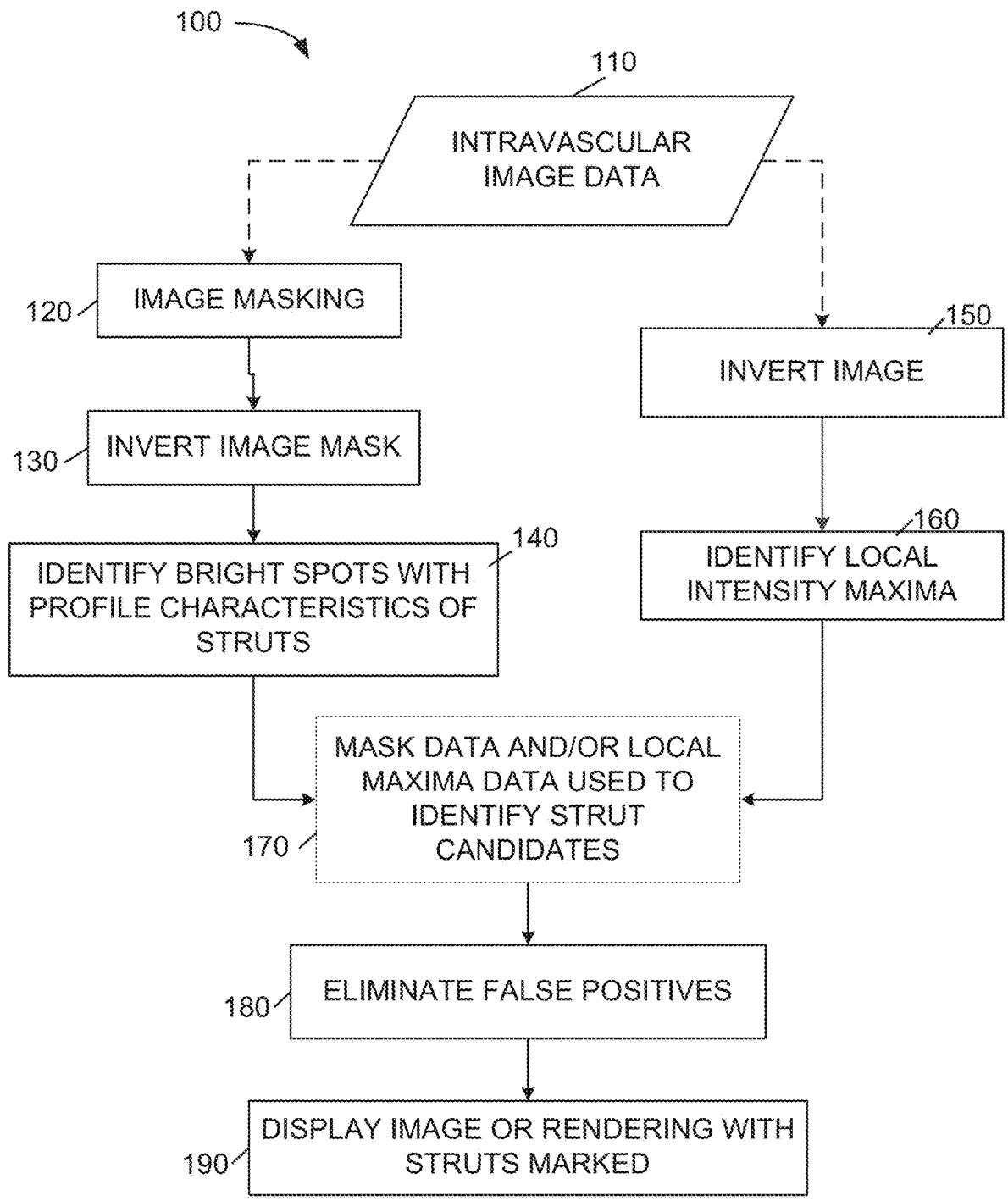
FIG. 1C is a flow diagram depicting a process flow for BRS strut detection and resorption monitoring according to an illustrative embodiment of the disclosure.
Figure 1D:
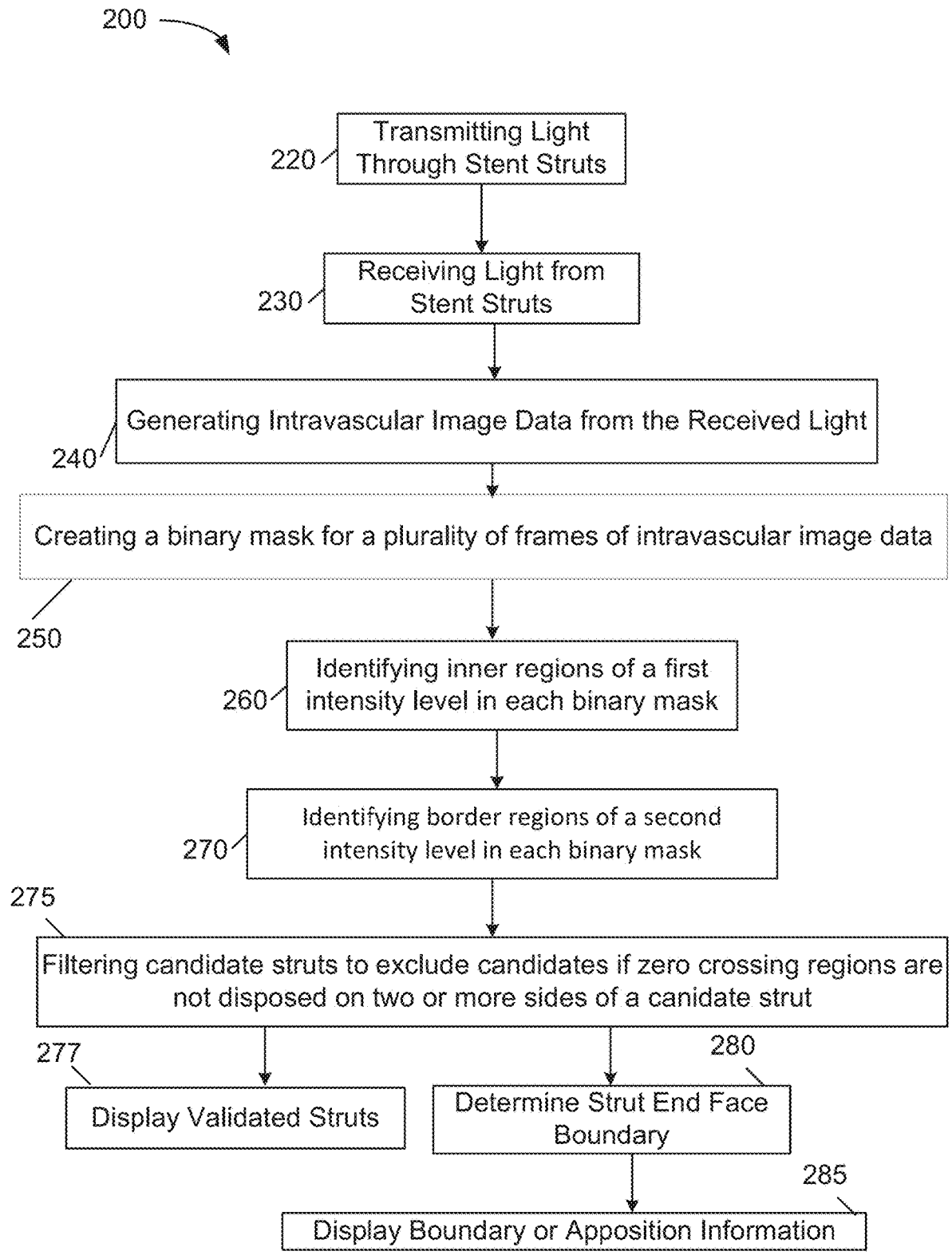
FIG. 1D is a flow diagram depicting process flow for BRS strut detection and strut apposition evaluation according to an illustrative embodiment of the disclosure.

FIG. 1C is a flow diagram depicting process flow for BRS detection and resorption monitoring. Another exemplary process flow for BRS detection is shown in FIG. 1D. A BRS can include a stent, a scaffold, or a component thereof such as a strut, edge, or other image able or detectable element thereof. Referring to FIG. 1C, the method 100 analyzes intravascular data 110 to identify BRS profiles. The intravascular data can include OCT data. The OCT data can include scan lines, 2D polar images, 2D cross-sectional images, and frames of images data that include or that are generated using the foregoing.

In various embodiments, the method uses image masking to identify or enhance a BRS. In various embodiments, the method uses relative or local extremum such as local intensity maxima to identify BRS. In some embodiments, the method uses a hybrid approach, combining information from image masking with information about local intensity maxima, to increase detection accuracy. It is worth noting that the masking and intensity processes described herein can be reversed with high and low intensities being swapped for low and high intensities. The processing using high or bright intensity for interior of BRS struts does result in more accurate results with less candidates being excluded during validation in some embodiments.

Figures 2A, 2B:
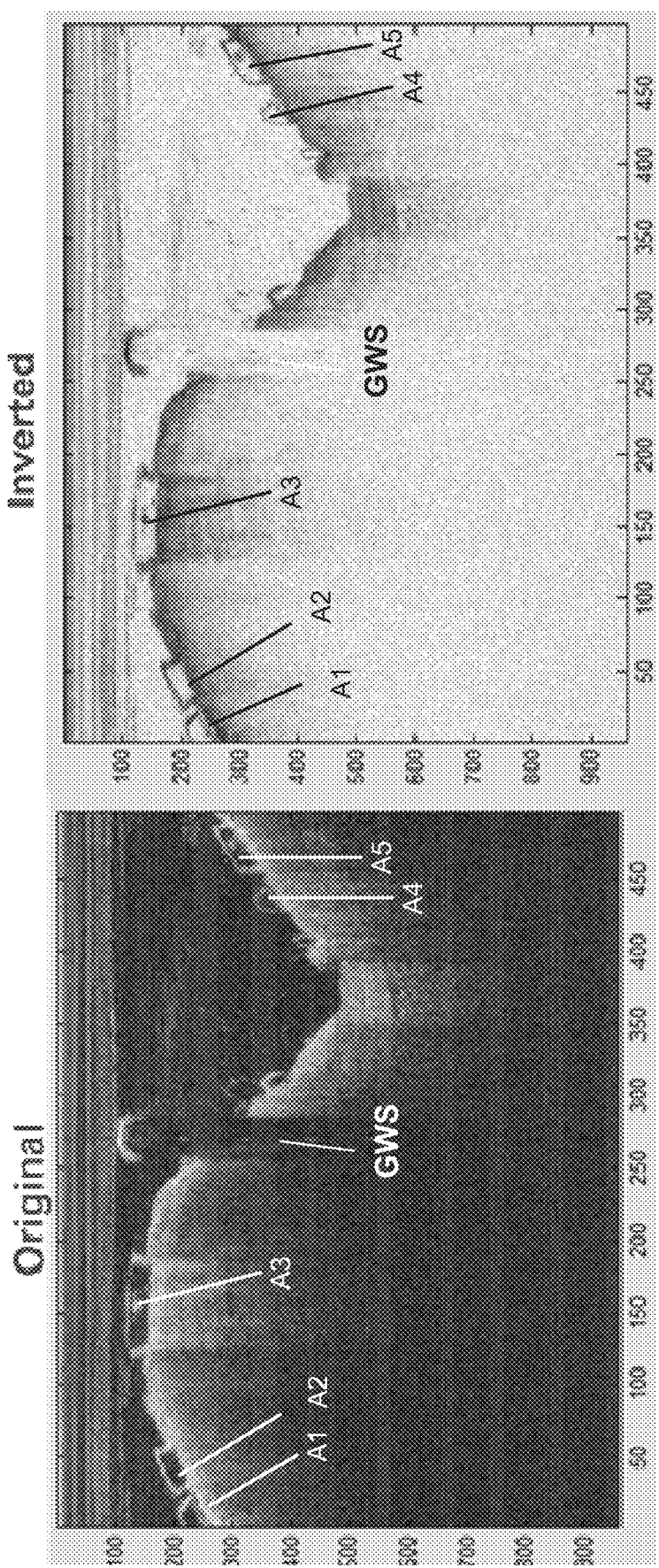
FIG. 2A is a scan line OCT image of a vessel that includes a BRS scaffold according to an illustrative embodiment of the disclosure.
FIG. 2B is an inverted image of FIG. 2A according to an illustrative embodiment of the disclosure.

FIG. 2A shows a raw scan line OCT image prior to inversion and FIG. 2B shows the same scan line OCT image after image inversion. Inversion converts the dark inner stent regions to light inner stent regions. This is important because the inner region of BRS have a higher density of local maxima responses in inverted OCT images. For reference, various inner regions of BRS struts are shown A1, A2, A3, A4 and A5. This results in an increase in resolution and detection accuracy for BRS detection.

Figure 3B:
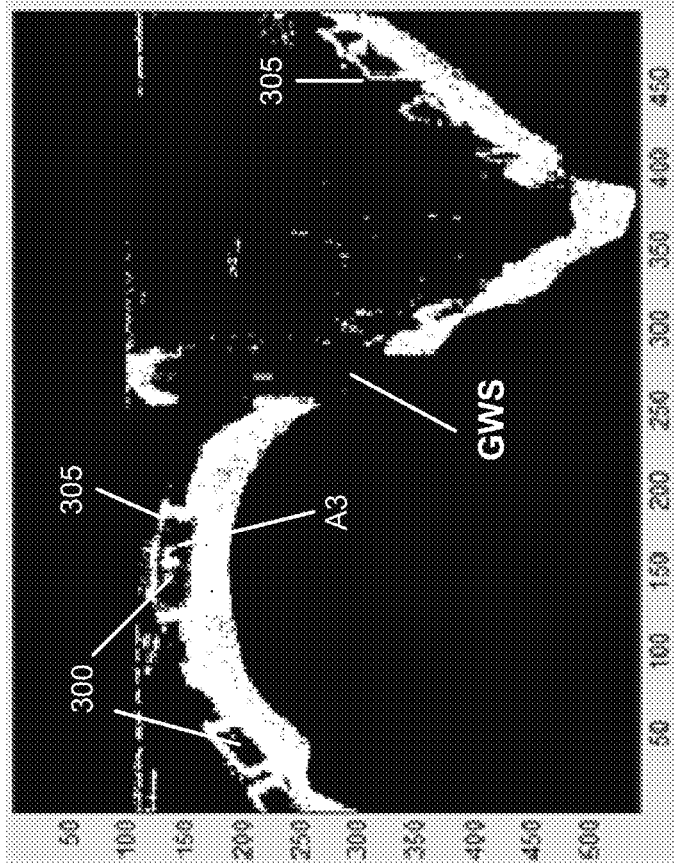
FIG. 3B is a mask image of FIG. 3A according to an illustrative embodiment of the disclosure.
Figure 3A:
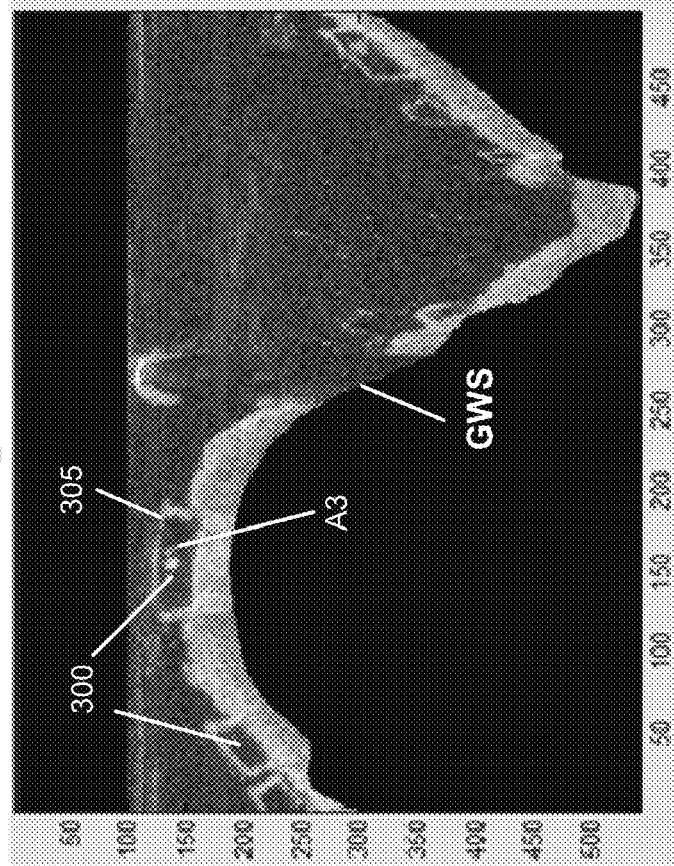
FIG. 3A is a scan line OCT image of a vessel that includes a BRS having struts according to an illustrative embodiment of the disclosure.

At step 120 of FIG. 1C, image masks are created from raw OCT images. FIG. 3A is a subset of FIG. 2A with strut A3 shown for reference. The inner portion 300 of some exemplary BRS struts and the outer border 305 is visible. FIG. 3A shows a raw scan line OCT image prior to image masking. In various embodiments, portions of the vessel lumen (image top) and vascular tissue (image bottom) can be redacted or ignored to reduce data processing and noise in subsequent steps. FIG. 3B shows an image mask of scan line image shown in FIG. 3A. In FIG. 3B, the contrast between inner region 300 and outer border 205 for a given strut is sharper and emphasized as a result of the masking. The masking can be implemented using binarization based on an intensity threshold.

Figure 4A:
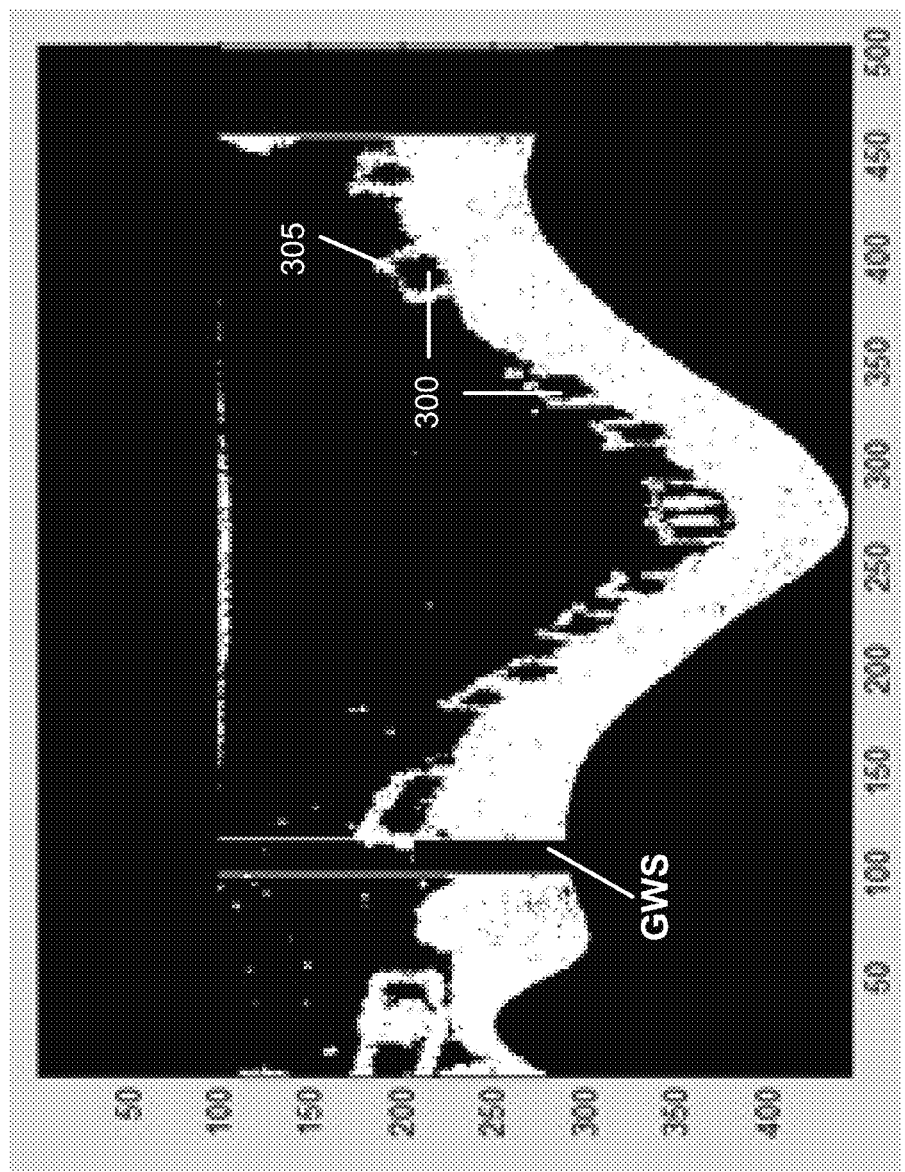
FIG. 4A is a mask image of a vessel that includes a BRS having struts according to an illustrative embodiment of the disclosure.
Figure 4B:
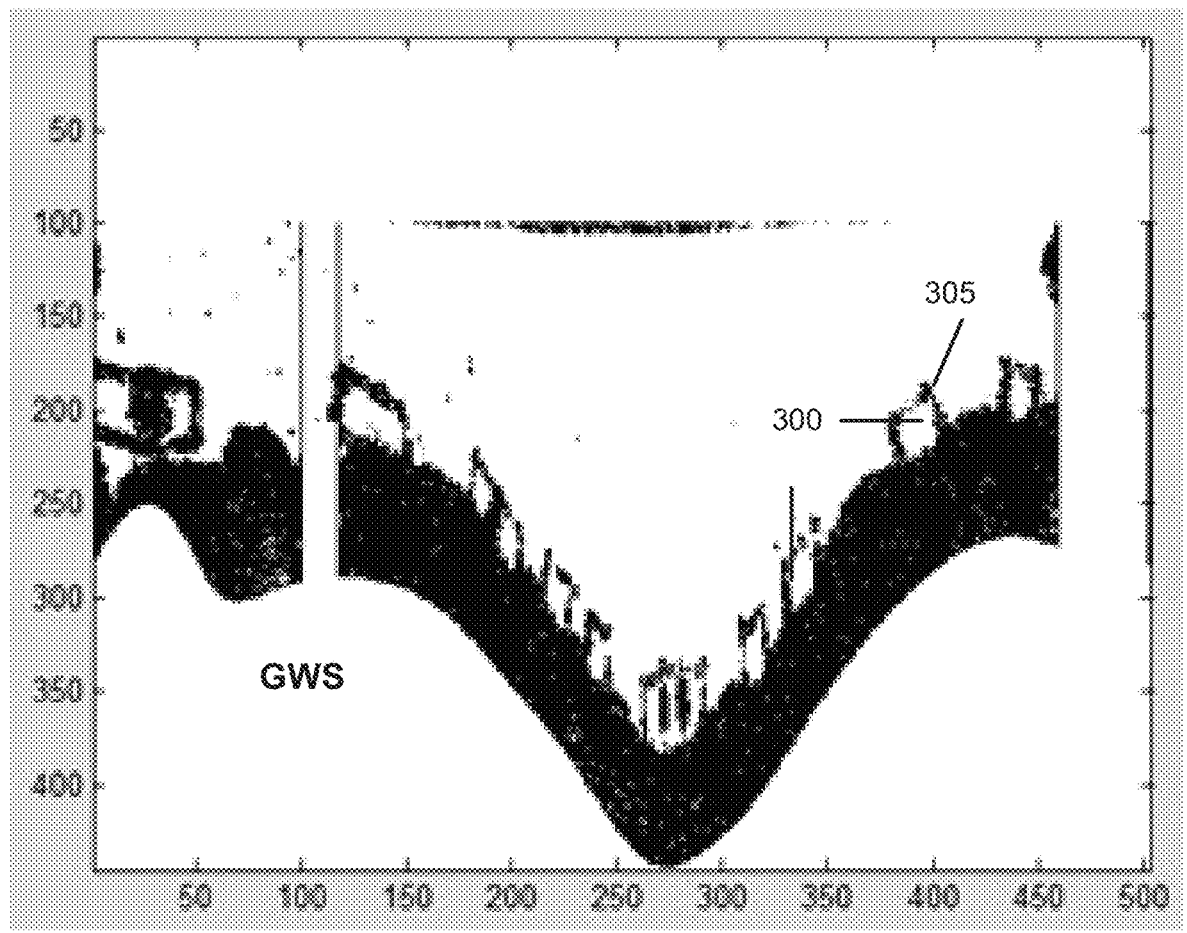
FIG. 4B is an inverted image of FIG. 4A according to an illustrative embodiment of the disclosure.

At step 130 of FIG. 1C, the image mask prepared in step 120 is inverted. Inversion maps light areas to dark and dark areas to light, which results in the inner strut regions appearing light and the outer strut regions appearing dark. In this way, high intensity or bright regions corresponding to cores of BVS are appear as bright insular regions relative to a low intensity/dark background. The inner regions of candidates BRS appear as bright or luminous as a result of the inversion of the image. FIG. 4A is a scan line mask image, with portions of the lumen and vascular tissue redacted. FIG. 4B shows an inverted mask image of FIG. 4A.

At Step 140 of FIG. 1C, the inverted image mask prepared in Step 130 is processed to isolate the bright inner strut regions created by the inversion process. The inverted mask is processed using morphological processing to isolate bright spot islands that have sizes and profiles characteristic of BRS. These bright spots correspond to signal or foreground as a result of the inversion process. The typical boundary size of a freshly implanted stent ranges from about 2 to about 4 microns (see image below). The strut size itself may vary given that it is a continuous feature and the system used is imaging slices of it. In one embodiment, a BRS detection method isolates all connected regions or islands less than about a predetermined search region. In one embodiment, this region is about a 50 micron×50 micron region. In one embodiment, the region is less than about 100 microns×100 microns. In one embodiment, the region is less than about 75 microns×75 microns.

Figure 5:
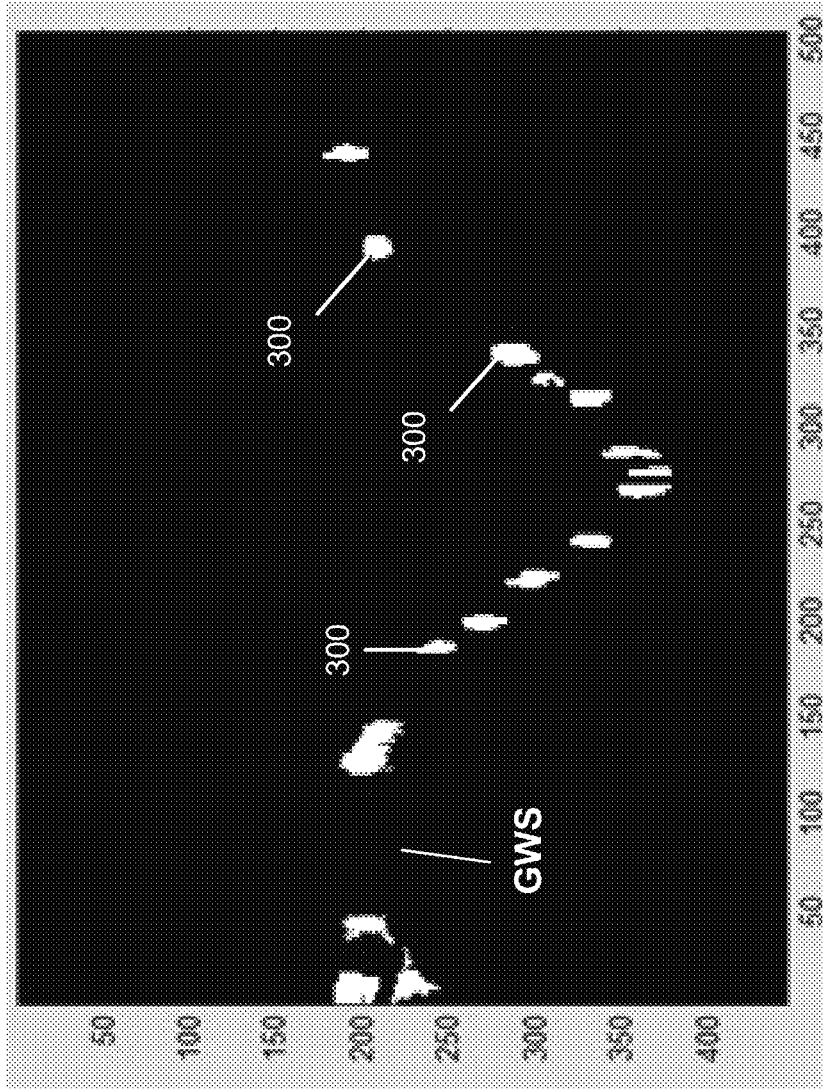
FIG. 5 is an inverted mask image filtered to isolate putative BRS struts according to an illustrative embodiment of the disclosure.

In one embodiment, the region is less than about 60 microns×60 microns. In one embodiment, the region is less than or equal to about 50 microns×50 microns. One or more morphological filters are applied to detect struts of different sizes. In one embodiment, a Gaussian filter or a Laplacian of a Gaussian filter is used as a morphological filter. Two or more such filters are used in one embodiment. FIG. 5 is an inverted mask image that has been filtered to isolate candidate inner strut regions 300. These bright insular regions stand out relative to the dark background which is effectively without signal, while the candidate inner regions 300 are signal containing regions. Each bright spot corresponds to a potential inner strut region. The spots are formed from a plurality of bright pixel regions. The process of generated an inverted mask image helps solve the problem of detecting BRS. Instead of using detectors to look for an edge of scaffold corresponding to a polymer or coated material, a high intensity or bright region is generated for each candidate BRS by the inversion process. As discussed herein, shifting to a bright intensity facilitates comparing bright pixels relative to each other to define boundary of inner BRS region.

Figure 6A:
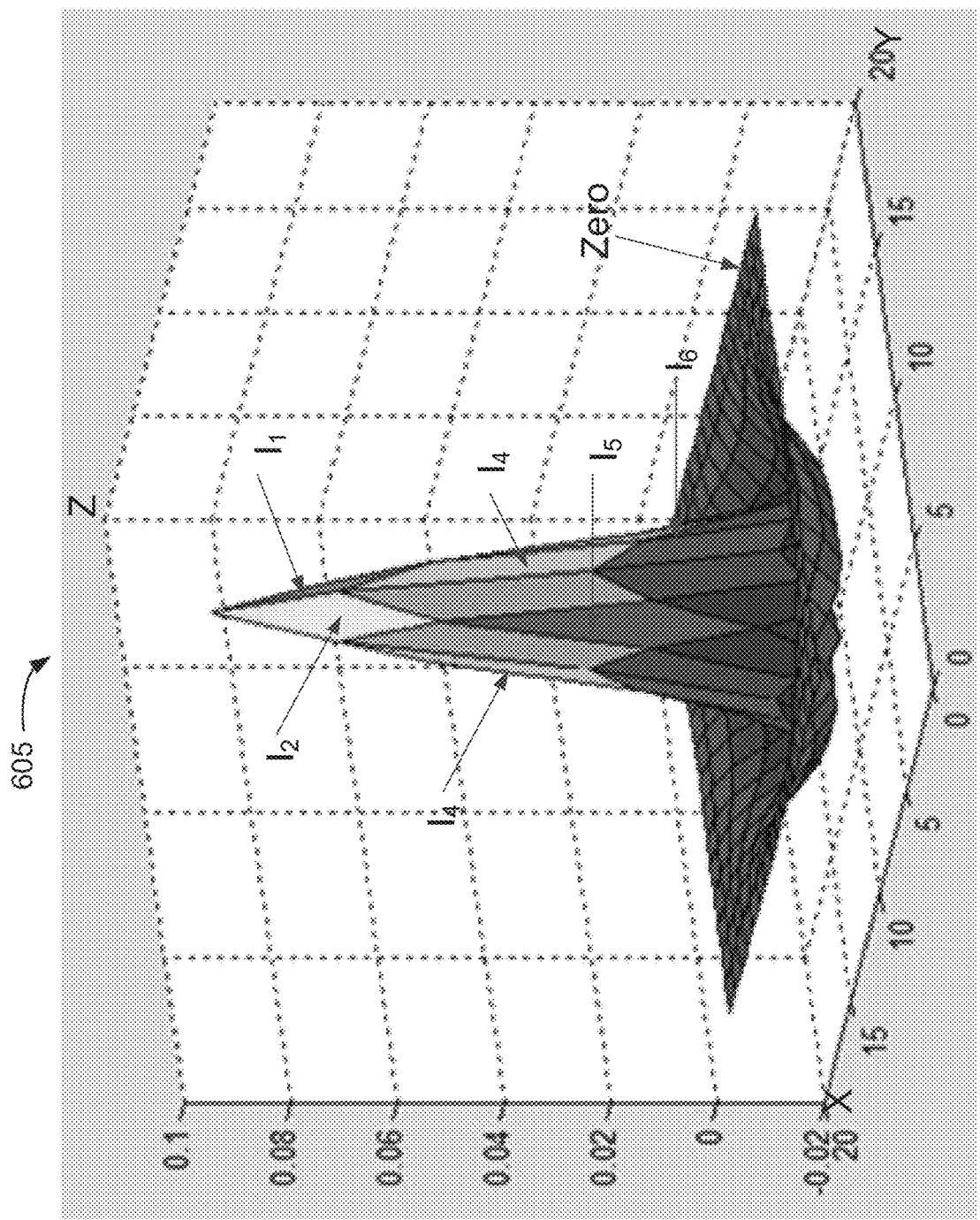
FIG. 6A, FIG. 6B, and FIG. 6C are filters with different parameters according to an illustrative embodiment of the disclosure.
Figure 6B:
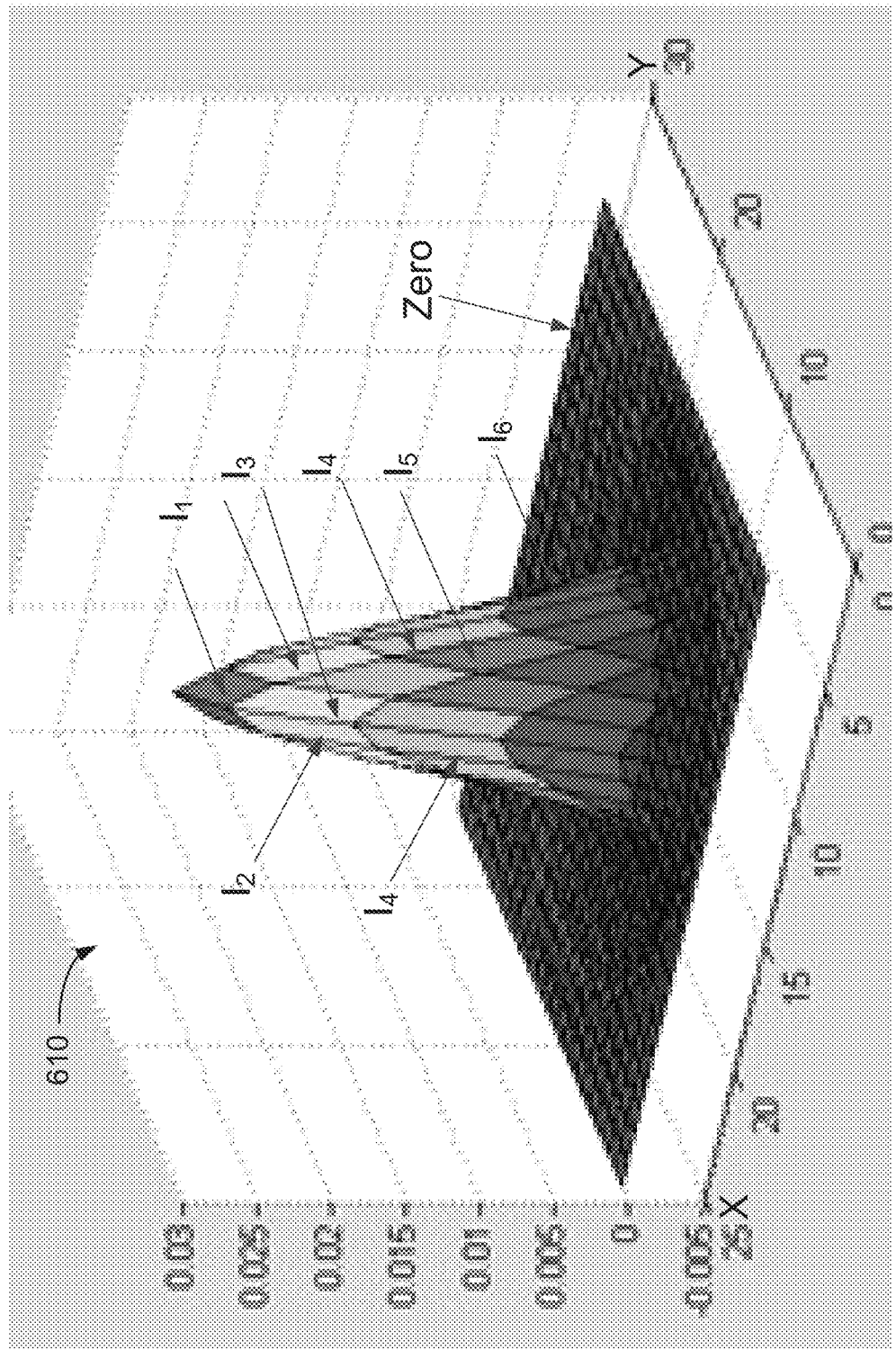
Figure 6C:
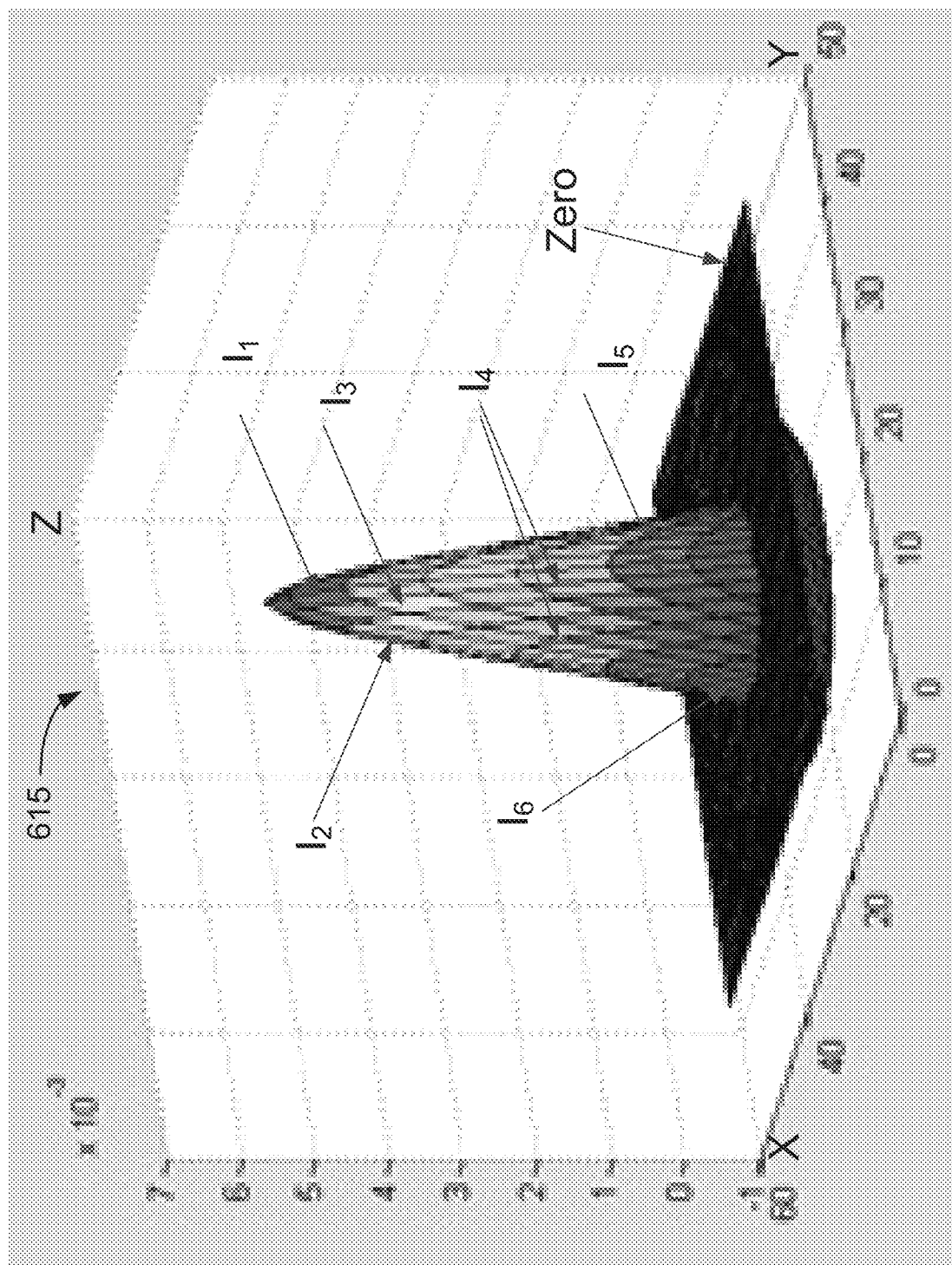

FIG. 6A, FIG. 6B, and FIG. 6C are depictions of a Laplacian of Gaussian filters with different parameters, for detecting bright spot islands in inverted mask images. The three filter responses 605, 610 and 615 have different shapes and vary based on the underlying intensity values shown. The vertical axis is a z-axis Z in one embodiment. The x-axis X and the y-axis Y define a two dimensional space. In general, the filter have the shape of a Gaussian or a transformed Gaussian. This two dimensional space corresponds to the spatial dimensions of a frame of image data with the z value or height corresponding to the intensity value associated with a pixel or region. For the various filters shown, the z-values vary over a range of different intensities. Exemplary intensity levels I1 to I6 are shown. Other gradations and in between intensity values are shown by the color transitions between the labeled intensity. In one embodiment, the x-axis and the y-axis correspond to the rows and columns of a matrix. With respect to this matrix, a z-axis value is an intensity value at a given row or column of the matrix.

Thus, in one embodiment, values I1 to I6 are values of the matrix. The color values of the intensities are highest at the red color indicators, then orange, then yellow, then light blue, blue, and then dark blue is effectively the floor at intensity zero. The values along the z-axis, which are shown as various heights or lengths, correspond to an intensity value that can be selected for one or more BRS. In one embodiment, the z-axis values are the magnitude of the filter. In one embodiment, the response of the filter will correspond to the contrast and shape of one or more BRS.

The filters depicted in FIGS. 6A-6C are templates that can be convolved with the raw image to produce a filter response. In FIGS. 7A and 7B, the green dots 700 depicted are the peaks of the filter response overlaid on the original image. The struts appear in different shapes and sizes and in different intensity variations. The dots can be analyzed to form groupings G1, G2, G3 as shown and discussed in more detail below. Some struts can have a strong contrast between their inner and outer boundary layers while others may not. To capture this variation, different filters can be designed based on various intensities or strut sizes. The peaks and the shapes of the filters correspond to the features they would be highlighting in the strut region. Thus, the values I1 to I6 (and other in between intensity values) can be adjusted over a range of possible struts that may be encountered and detected in spite of their size or intensity variations.

Multi-resolution filtering is performed to detect or identify isolated or bounded bright regions in the intensity-inverted image. It should be understood that these bright regions or islands can also be detected by reversing the intensity levels used such that the border of the islands is darker and the inner region become bright and other different intensity gradients can be used so long as the differing intensities can be resolved relative to each other. That is, islands or isolated regions with a first inner region having a first intensity and an outer border region or edge having a second intensity level are identified using one or more detection methods of the disclosure. In one embodiment, the first intensity is greater than the second intensity. In one embodiment, the second intensity is greater than the first intensity. In one embodiment, a bright pixel or a luminous pixel is a pixel having a first intensity that is greater than a second intensity, wherein the second intensity is the intensity of a dark pixel. The luminous or bright pixels are foreground/signal containing. The dark/black regions effectively become a signalless background for the insular regions to appear relative to in the processed images.

One or more filters are used to highlight bright intensity regions surrounded by dark intensity regions (or vice versa when the inner intensity regions are dark and surrounded by relatively brighter intensity regions). In one embodiment, the filters are Laplacian of Gaussian (LoG). In one embodiment, edge detection, zero crossing, and other filters can be used to identify the appearance of a BRS in an OCT image as described herein. As shown, in FIGS. 3A, 3B, 4A, 4B, 5, 8A, 8B, 8C, 9A, 9B the dark regions 300 and the light regions 305 are arranged in bordered box or isolated region. Specific filter parameters are designed based on the shape and size of the BRS to highlight region of interest. These filters are exemplary only, and additional LoG filter parameters can be used to identify bright spots having size and/or shape characteristics of BRS interior regions. Identified bright spot islands are subsequently vetted, as discussed more fully herein, to identify candidate struts.

In addition to image mask inversion, the original OCT image can be processed to identify local intensity maxima in regions likely to contain BRS (e.g., near the blood vessel wall). Before local intensity maxima can be detected, at Step 150 the raw OCT image is inverted to map light areas to dark and dark areas to light.

FIGS. 2A and 2B are used to detect local intensity maxima as described in step 160 of FIG. 1C. At Step 160 of FIG. 1C, the inverted OCT images from Step 150 are processed to identify local intensity maxima. In one embodiment, local intensity maxima or relative extremum are identified by performing a scan of the intravascular data. The scan is performed within a neighborhood or region. In one embodiment, a cross neighborhood is used. In one embodiment, a circle neighborhood is used. In one embodiment, a square neighborhood is used. The scan can be a raster scan or a per pixel scan or other image directed scans or pattern recognition methods in one embodiment. The intravascular data can include two-dimensional data such as a polar or coordinate image for a given frame of the pullback. The intravascular data can include scan lines that are used to generate an intravascular image.

In one embodiment, if an arrangement of nine pixels is grouped in a cube configuration, such that the central pixel is the pixel under evaluation for being a local maximum, the intensity of the central pixel is compared to the intensities of the other eight pixels. In turn, in one embodiment, such as central pixel is selected as a local maximum if its intensity is greater than the other pixels. This cube neighborhood and the other neighborhoods are used to compare one pixel to the other pixels that are grouped with it to define the neighborhood based on intensity level. As part of this scan or search for relative extremum such as local maximum, the software-based method, such as implemented with a BRS detection module 44a, generates an output table of local maximum identified. If no pixels are larger than the current pixel, than the current pixel is local maximum.

In one embodiment, a cross neighborhood is used. In one embodiment, a circle neighborhood is used. If there are no pixels in a neighborhood with an intensity greater than a pixel being evaluated, the pixel being evaluated is categorized as a relative or local extremum such as a local maximum. The reference to local maximums can also be applied to designs in which the underlying images or signals are inverted such that a local minimum is indicative of an inner region of a BRS. In one embodiment, if one pixel intensity is higher than the pixel under evaluation, then that pixel is then evaluated relative to the other pixels that neighbor the pixel being evaluated, and this process continues substantially until all of the pixels are evaluated.

FIG. 7A is a scan line OCT image of a BRS stented vessel with local maxima of the filter responses overlaid on the original scan line image. The blood vessel lumen and vascular tissue can be redacted or ignored to reduce noise. The lumen and lumen boundary LB are shown. The intravascular probe use to generate the image would be disposed in the lumen. As demonstrated by FIG. 7A, local intensity maxima are clustered within inner BRS regions and therefore can serve as markers for candidate struts. The detected BRS strut regions are labeled as groups G1, G2, and G3 for clarity in FIG. 7A. The groups or clusters are formed in the inner region 300 and bounded by the outer portion of the strut 305.

FIG. 7B is a zoomed in version of FIG. 7A with the addition of boundary 35 of strut end faces shown by the dotted line in the upper portion of the figure. The arrows G1, G2, and G3 each point to an end face of each respective strut that is tissue facing as shown. Local intensity maxima 700 (also shown by clusters of green dots) can be used alone or in conjunction with bright spot islands/detection of regions 305, as discussed more fully herein, to identify candidate struts.

At Step 170 of FIG. 1C, the bright spot islands and/or local intensity maxima are used to identify candidate struts. In preferred embodiments, information from both the inverted mask and the local maxima is combined to detect strut candidates. Bright spot islands in the inverted mask that coincide with clusters of local intensity maxima are deemed to be candidate BRS.

At Step 180 of FIG. 1C, candidate struts are optionally evaluated such as through a validation process to eliminate false positives. In one embodiment, feature analysis is performed to eliminate false positives. This is one approach to BRS strut validation. In one embodiment, a shape, a thickness, intensity profile, zero crossing, intensity patterns, or other feature of BRS is used to invalidate a candidate BRS. In this way, false positive detections of candidate BRS struts can be achieved.

An example of a feature which can be detected and analyzed is a zero crossing feature. BRS appear as hollow boxes in original, raw OCT scans, with a dark strut interior region surrounded by a light border on all sides. Thus, a zero crossing filter can be used on original intensity images to confirm that each dark strut interior region is bordered on all sides by a light (i.e., zero-crossing) region. In other embodiments, a zero crossing filter can also be used to detect BRS in which an inner light region is bordered by dark regions.

As will be appreciated, a zero crossing filter can be applied to an inverted raw image, an image mask, or an inverted image mask because of the intensity contrast between BRS interior regions and border regions. Strut candidates that do not border a zero-crossing region on all sides are eliminated.

Figure 8A:
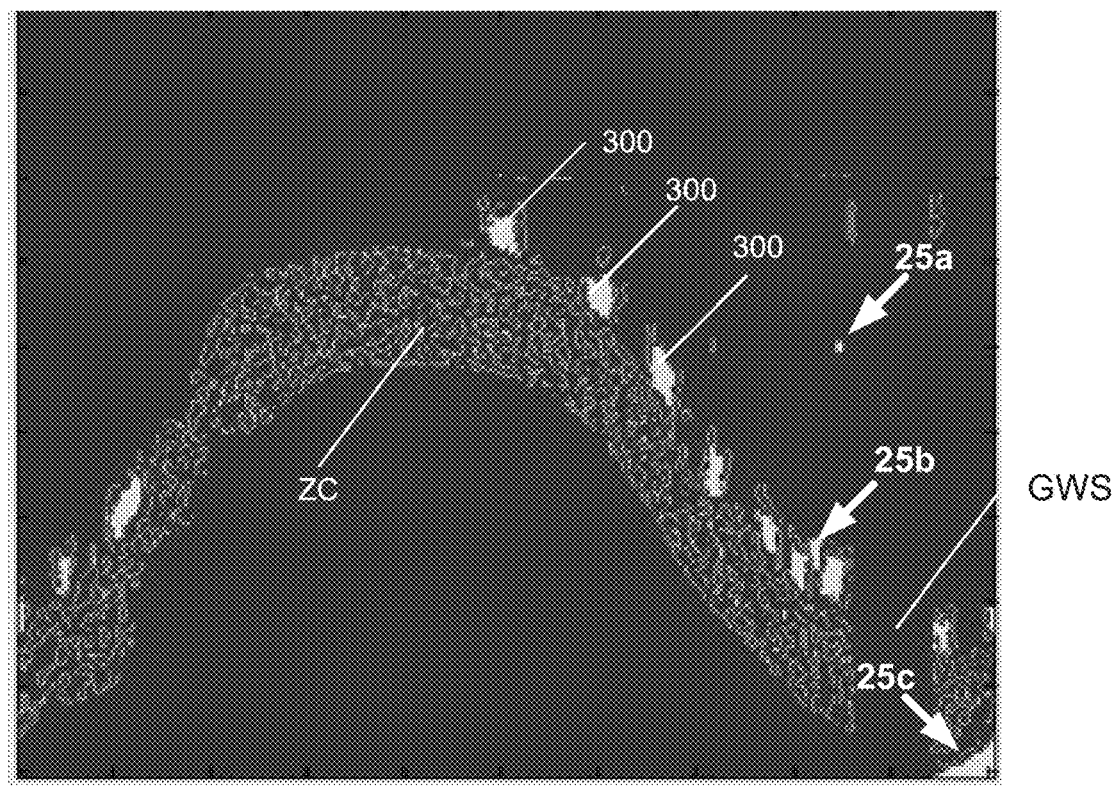
FIG. 8A is a rendered scan line image of a vessel that includes a BRS having struts before zero crossing filtering according to an illustrative embodiment of the disclosure.
Figure 8B:
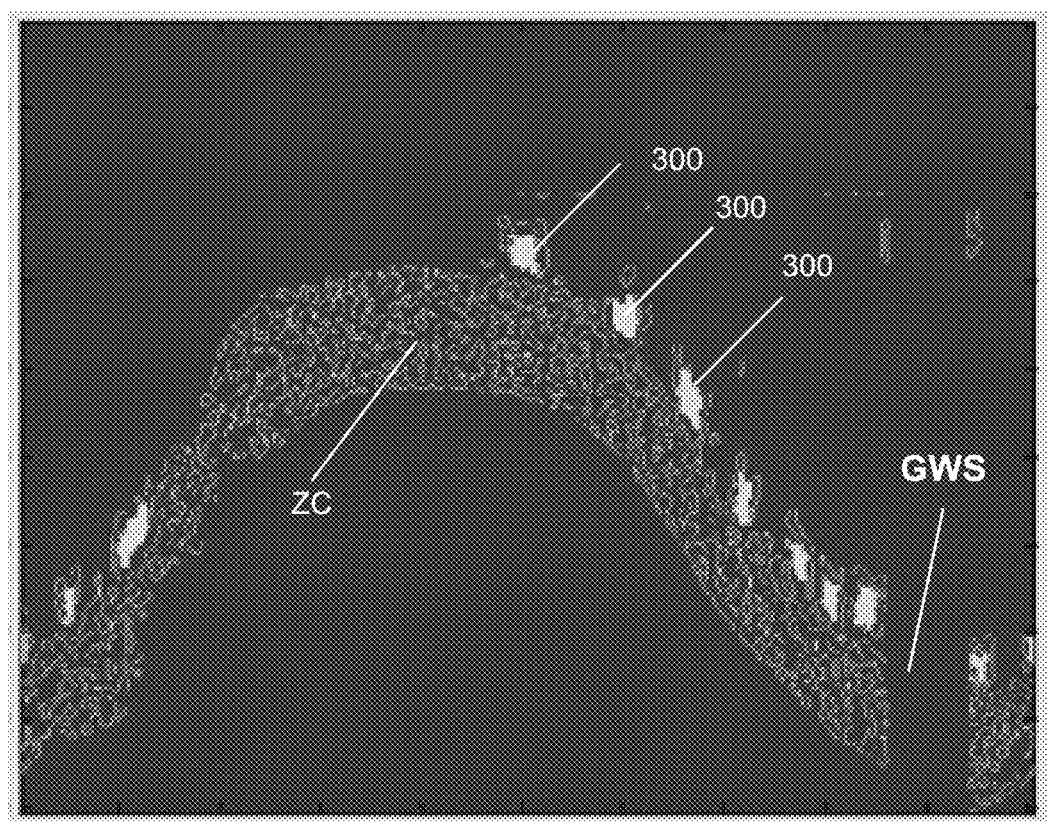
FIG. 8B is a rendered scan line image of a vessel that includes a BRS having struts after zero crossing filtering to remove false struts according to an illustrative embodiment of the disclosure.
Figure 8C:
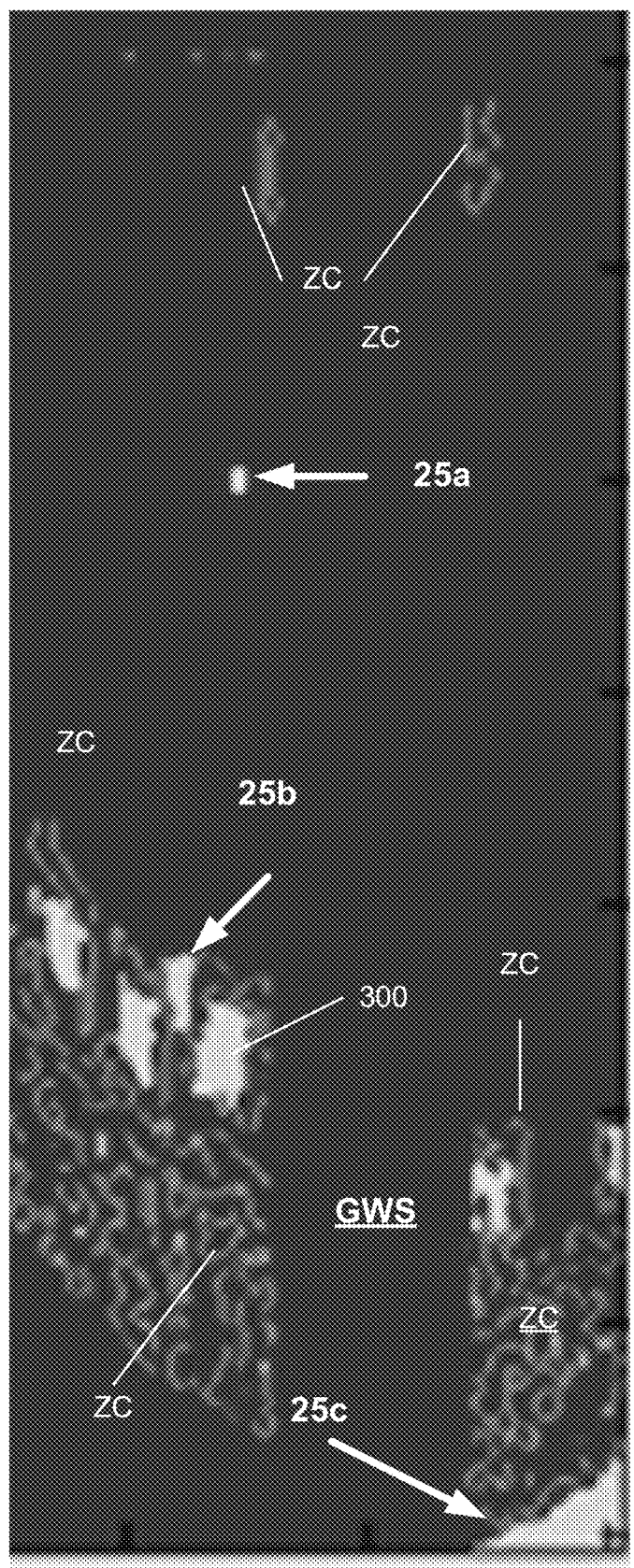
FIG. 8C is a zoomed in view of a portion of FIG. 8A showing three candidate struts of a BRS that are rejected during a feature-based detection validation step according to an illustrative embodiment of the disclosure.

FIG. 8A is a rendered scan line image of a BRS stented vessel before zero crossing filtering. The signature gap of the guidewire shadow GWS is also shown. The inner regions 300 of three exemplary valid struts are shown. These regions 300 are bordered on all sides by the squiggly lines in the image that denote zero crossing ZC. Three false positive candidate struts 25a, 25b, and 25c on the right side of the image near the GWS are not bounded on all sides by a zero crossing region ZC. As shown in FIG. 8B, these false positive struts 25a, 25b, and 25c are removed when the zero crossing filter is applied. In one embodiment, a zero crossing ZC must be detected near a candidate strut on its lumen facing and tissue facing side. FIG. 8C is a zoomed in view of a portion of FIG. 8A showing three candidate struts 25a, 25b, and 25c that are rejected during a feature-based detection validation step. In FIG. 8B, these candidates have been removed as a result of the zero crossing analysis.

In other embodiments, four zero crossing regions ZCs must be detected on each side of candidate strut for it to be validated. The lines in the ZC regions are zero crossing peaks. Candidate strut 25a is isolated and has no ZC regions near it. Candidate strut 25b does not have a ZC on its top lumen-facing surface. Candidate strut 25c only has a ZC on one side. Given the lack of two or more ZCs around each candidate, the three candidate struts 25a, 25b, and 25c are invalidated as false positives. In general, the yellow inner regions 300 shown are bordered by two or more ZCs to be validated in one embodiment.

Figure 9A:
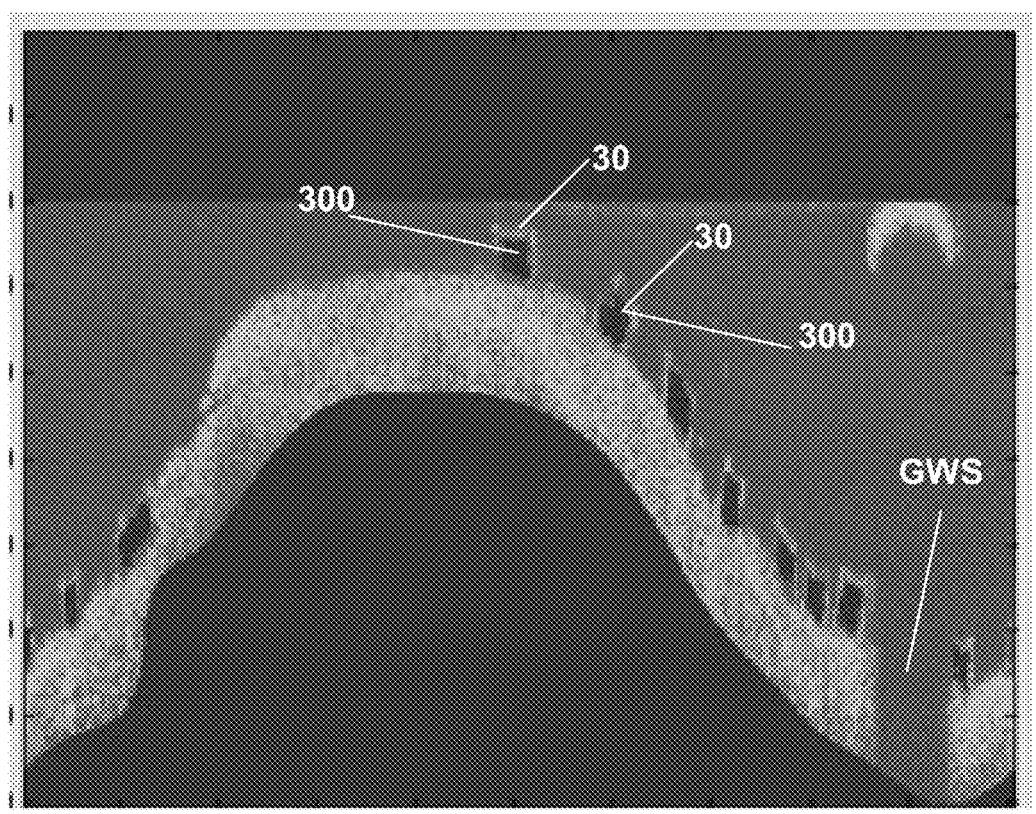
FIG. 9A and FIG. 9B are rendered scan line images of a vessel with detected struts highlighted according to an illustrative embodiment of the disclosure.
Figure 9B:
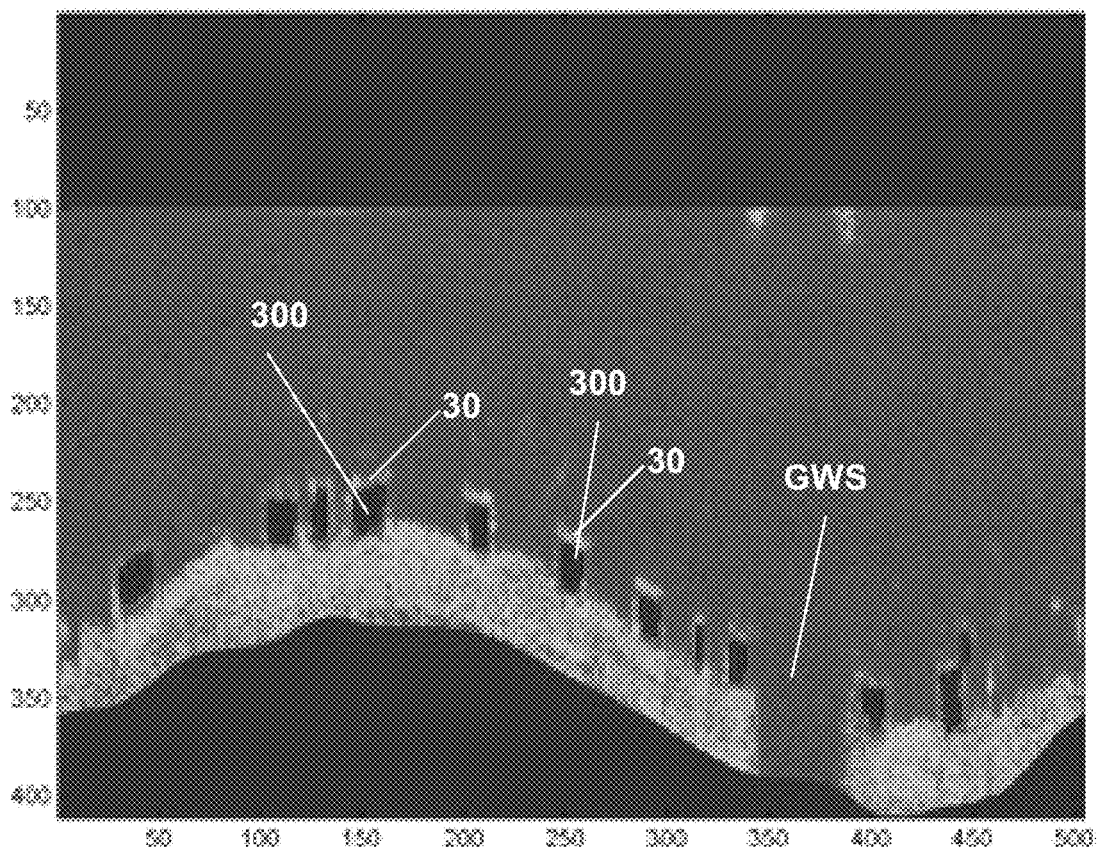

FIG. 9A and FIG. 9B are rendered scan line images of a stented vessel showing automatically detected and validated BRS in accordance with the method disclosed in FIG. 1C. The method of FIG. 1D can also be used. FIG. 9A is a modified version of 8A after false positive detection. FIGS. 9A and 9B are the original intensity values in polar space with the detection of inner regions 300 superimposed thereon. FIGS. 9A and 9B show the physical structure of the blood vessel in a polar view based on an OCT pullback through the vessel with the addition of valid struts 30. Zero crossing regions are detected relative to the position of inner region 300 and the valid struts 30 are displayed as a result of two or more zero crossing regions being present that border region 300.

Figure 10A:
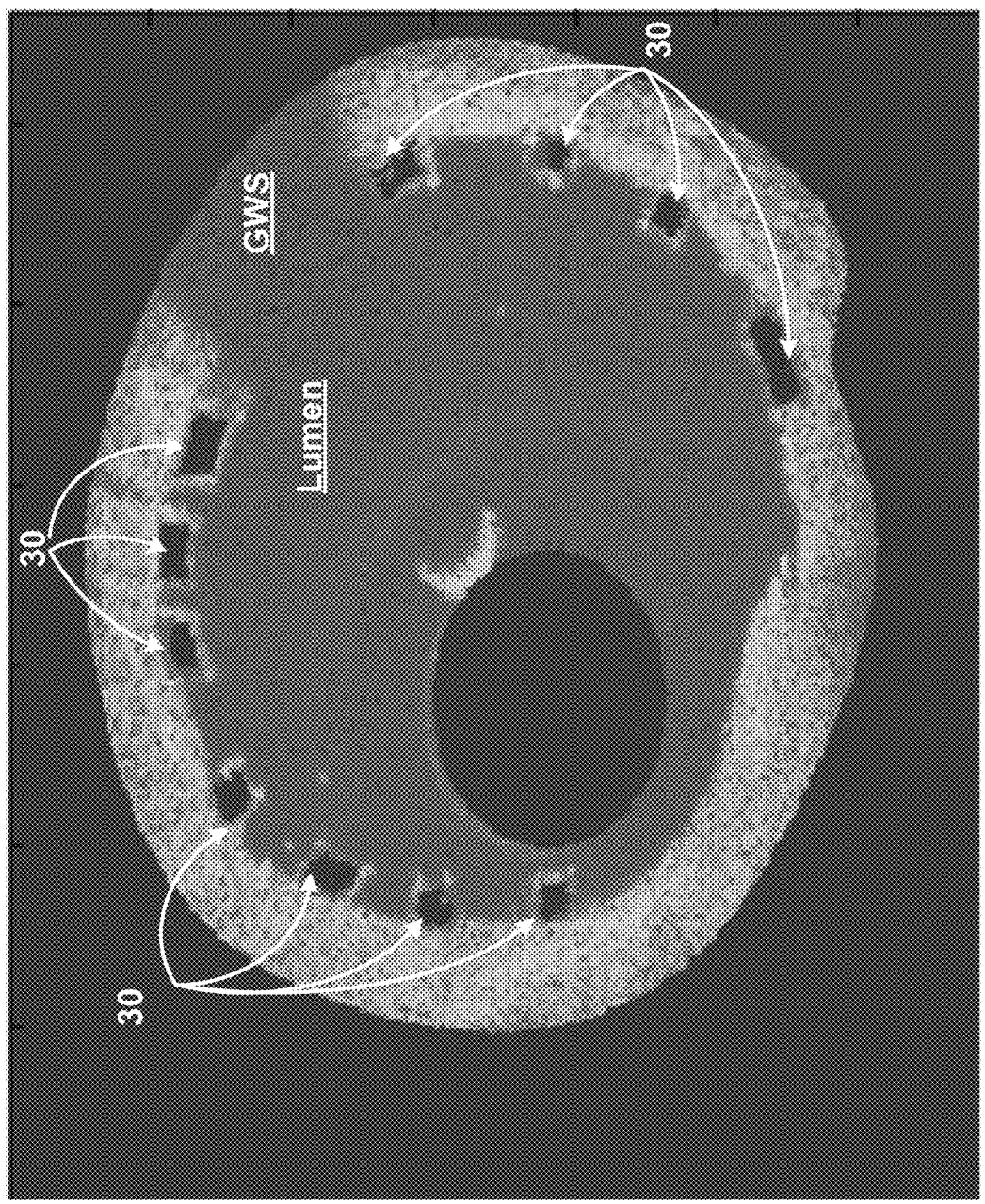
FIG. 10A is a cross sectional rendering of a blood vessel with detected struts highlighted according to an illustrative embodiment of the disclosure.
Figure 10B:
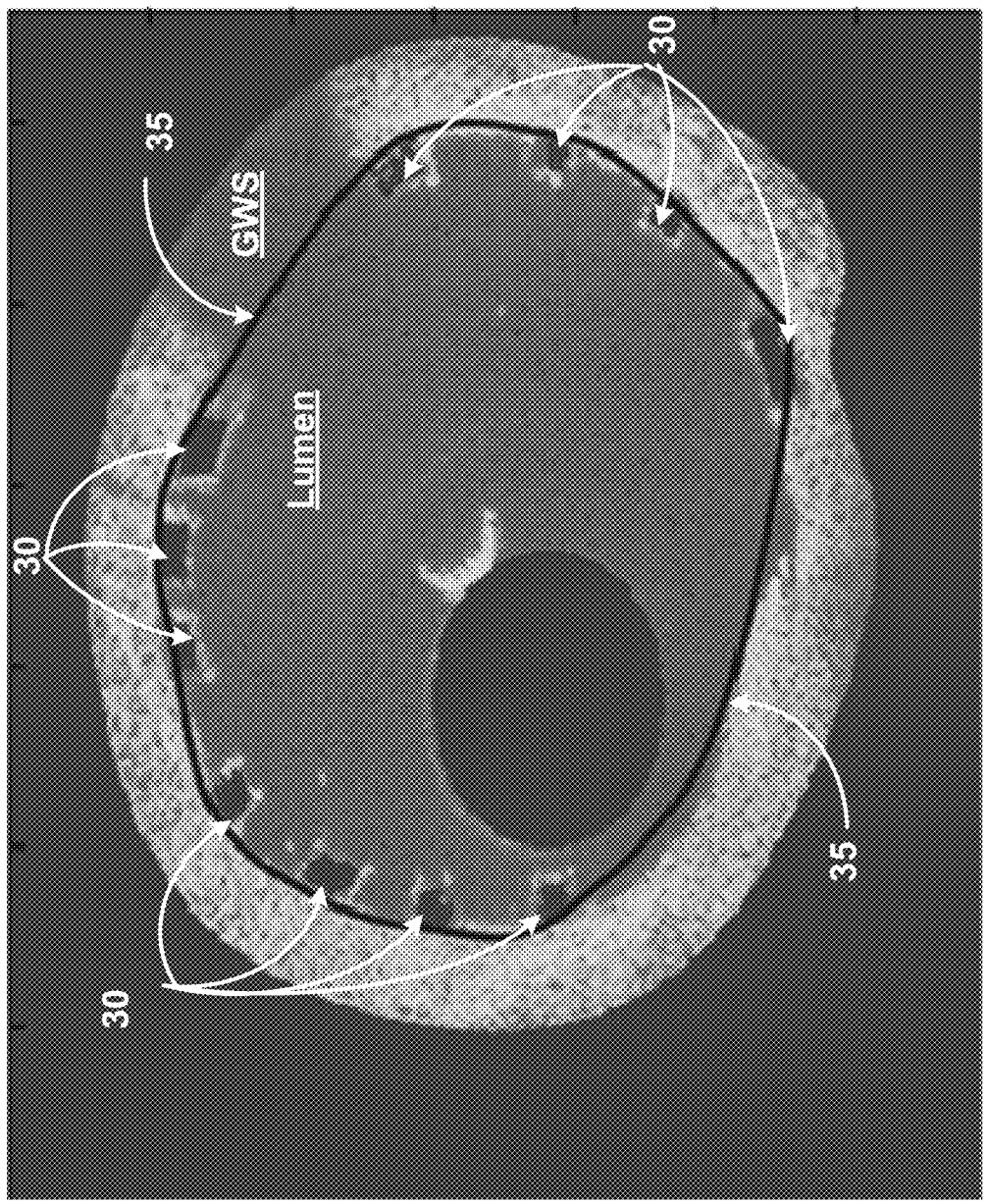
FIG. 10B is a cross sectional rendering of a blood vessel with detected struts highlighted and the tissue facing strut end face boundary or circumference is marked according to an illustrative embodiment of the disclosure.

At step 190 of FIG. 1C, the validated stents can be displayed on a graphical user interface, such as the scan line view shown in FIG. 8B. Validated struts also can be displayed in two dimensional cross sectional images, L-Mode images, or three dimensional views. For example, FIG. 10A shows a cross sectional rendering of a stented vessel with validated struts 30 highlighted. The GWS and lumen are also shown. FIG. 10B is a cross sectional rendering of a stented blood vessel with validated struts highlighted. After stent detection, a strut end face boundary 35 is detected using the edges of the struts oriented toward the blood vessel. The strut end face boundary 35 is displayed in FIG. 10A.

Figure 10C:
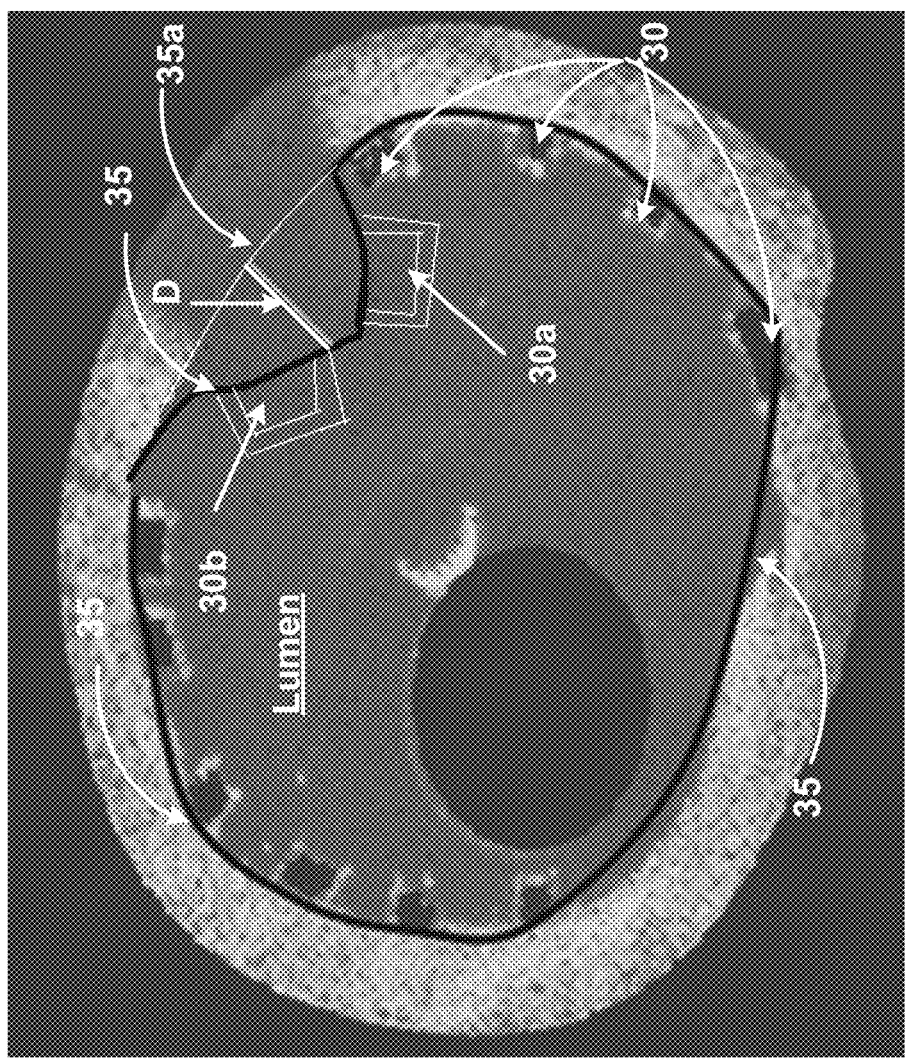
FIG. 10C is a cross sectional rendering of a blood vessel with detected struts highlighted and tissue facing strut end face boundary is marked showing strut malapposition or separation from the boundary according to an illustrative embodiment of the disclosure.

FIG. 10C is a cross sectional rendering of a blood vessel having a BRS with boundary or border 35 displayed on the image. As shown, strut end face boundary 35 has pulled away from lumen boundary 35a in the top right quadrant of the image. The back end of the detected strut locations are used to fit a contour that can be used to determine the strut cross section area. Some diagnosticians are interested in the strut boundary near the tissue. As a result, how far away strut end face boundary 35 is from the blood vessel wall which correspond to a lumen boundary 35a is of interest because it can indicate an improperly placed, underinflated, or other BRS related state that warrants further evaluation.

The lumen boundary 35a can be detected using the intravascular image data and image processing modules described herein. In addition, the distance D between the lumen boundary 35a and the tissue facing stent boundary 35 can be measured. This distance D can be displayed on a user interface. As shown, two validated struts 30a and 30b appear to have moved inward to the lumen away from the lumen boundary 35a. The ability to detect a BRS and determine the distance D is a useful diagnostic tool for end users.

FIG. 1D shows an additional generalized method 200 suitable for detecting struts or other components of a BRS deployed in a blood vessel. OCT is typically used to image the blood vessel, but other intravascular data collection modalities can be used in a given implementation. Optical imaging modalities are advantageous as they may have improved imaging capabilities relative to imaging techniques that are shadow dependent or otherwise work well with metal stents or stents with opaque components.

In one embodiment, the method includes the step of directing light to interact with strut Step 220. In one embodiment, the light interacts with the BRS. This interaction can include pass through a portion of the BRS. This interaction can include being reflected or modified by the BRS. This can be performed with an intravascular probe pullback through an artery and a given BRS disposed therein relative to the wall of the artery.

Without being held to a particular theory or mechanism, some of the light entering the BRS will be reflected therefrom and some of the light will pass through the BRS and be reflected back through the BRS from the wall of the blood vessel and returned to the intravascular data collection probe's sensors. Thus, the method can include receiving light from the struts of other components of the BRS Step 230. The sensors can include a beam director or a lens assembly for sending and receiving light in one embodiment. The method can include generating intravascular image data from the received light Step 240.

In addition, the method can include creating a binary mask for a plurality of frames of intravascular image data Step 250. The method can include identifying inner regions of a first intensity level in each binary mask Step 260. The method can include identifying border regions of a second intensity level in each binary mask Step 270. The method can include filtering candidate struts to exclude candidates if zero crossing regions are not disposed on two or more sides of a candidate strut Step 275. The method can include displaying validated struts Step 277. The first intensity level and the second intensity may correspond to the bright/signal intensities (foreground) and the dark/signalless intensities (background).

The method can include determining strut end face boundary Step 280. The method can include displaying strut end face boundary or apposition information Step 285. The distance D from lumen boundary 35a to BRS tissue facing boundary 35 can also be determined and displayed. In one embodiment, the distance D is representative of apposition level.

Automatic Quantification of BRS Resorption

BRS strut detection methods can also be used to monitor stent resorption over time. With the inner region of the strut segmented, the area of the strut in the post deployment can be compared with the area of the strut in periodic checkups to quantify resorption and/or resorption rate at one or more (e.g., 1, 2, 3, 4, 5, or more) checkup visits. BRS resorption can be analyzed on a per frame basis, a per stent basis, or a per strut basis, by way of non-limiting example. If the observed stent/strut resorption rate differs from the expected rate, or if a stent/strut is malapposed, the clinician also can intervene.

Figure 11A:
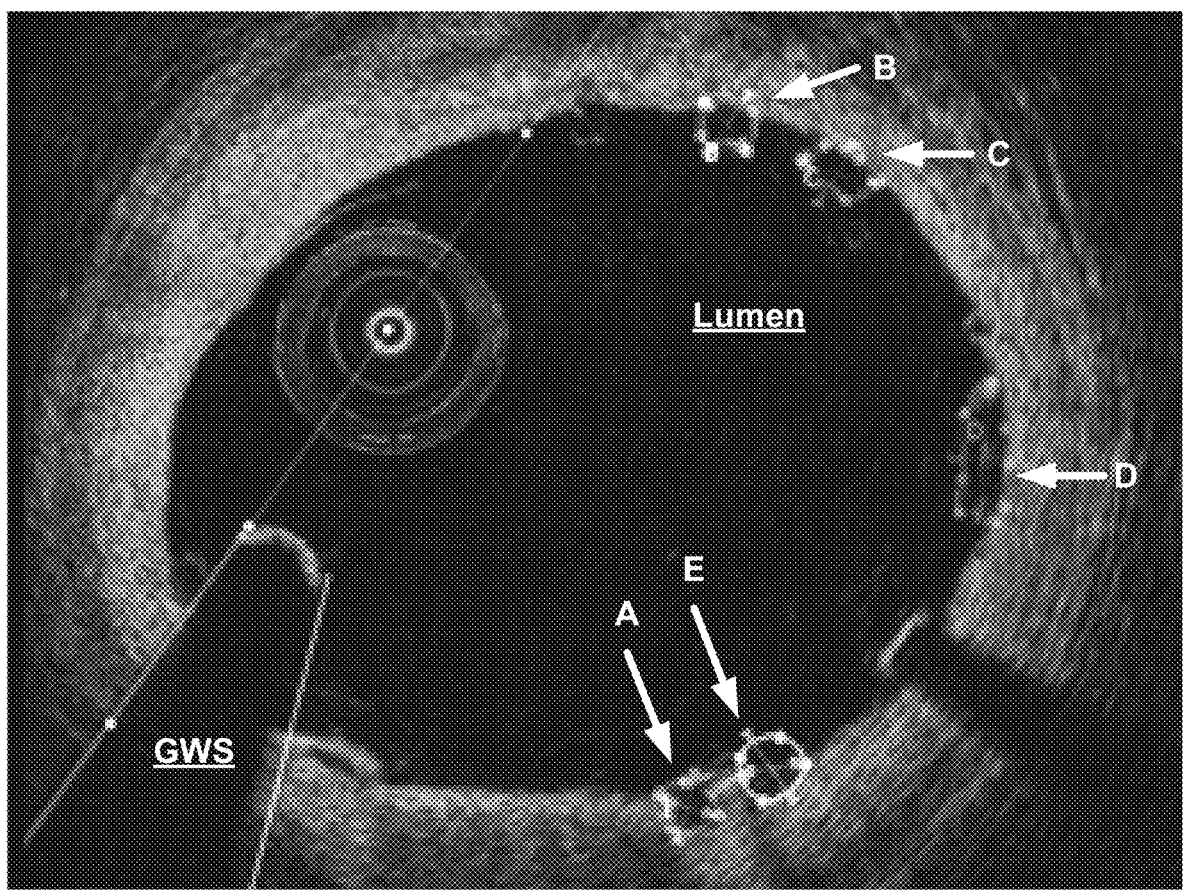
FIG. 11A is a cross sectional OCT image of a blood vessel obtained shortly after implantation of a BRS according to an illustrative embodiment of the disclosure.
Figure 11B:
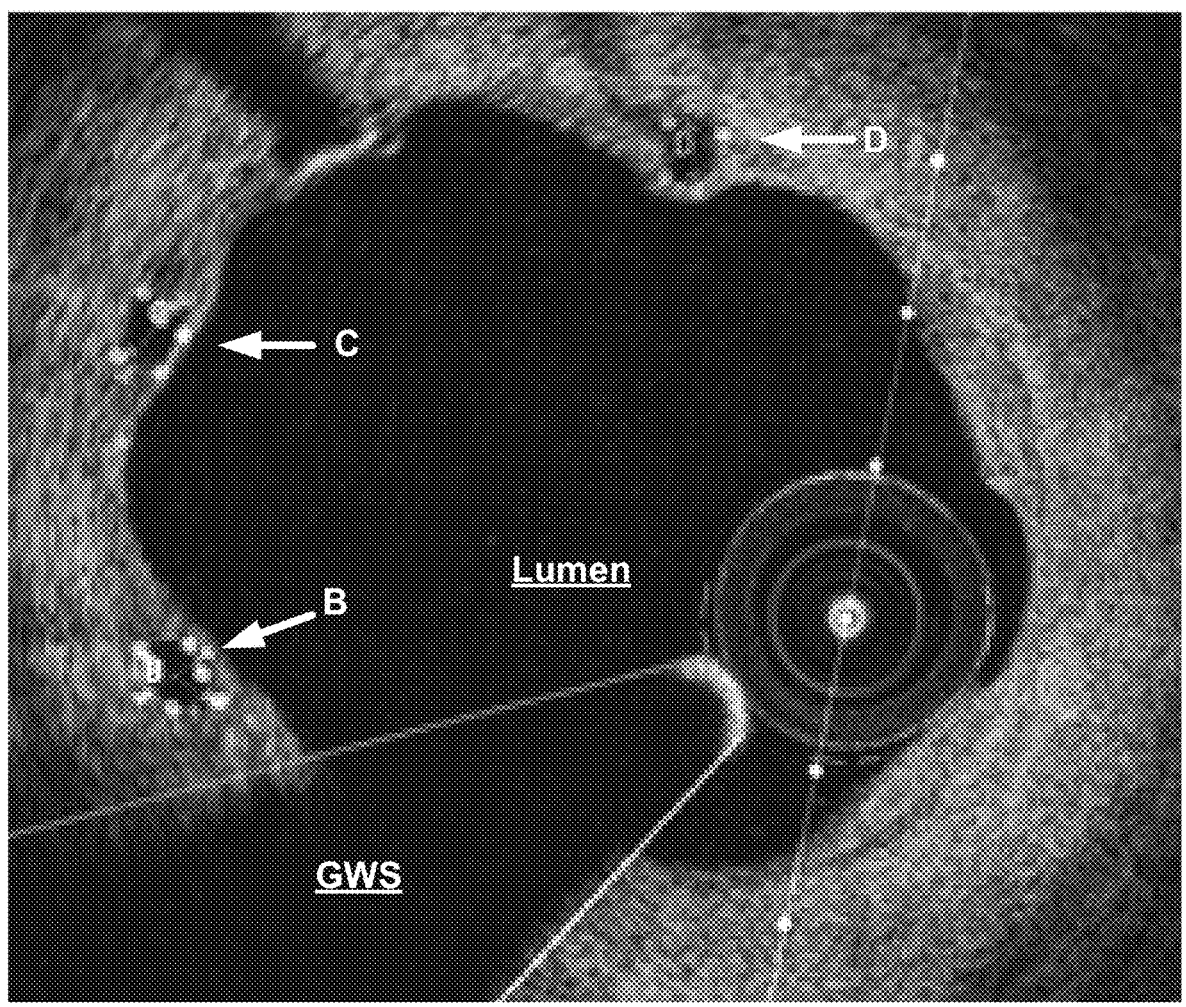
FIG. 11B is a cross sectional OCT image of the same BRS deployed region as FIG. 11A obtained 9 months later according to an illustrative embodiment of the disclosure.

FIG. 11A is a cross sectional OCT image of a stented blood vessel obtained soon after implantation of a BRS stent. FIG. 11B is a cross sectional OCT image of the same stented region as FIG. 11A obtained 9 months later. Frames are shown at the same location and are aligned using on a radio-opaque fiducial marker shadow seen in both images. Struts are outlined with polyhedrons to make the struts more visible and to facilitate calculation of strut size metrics or attributes. Struts can be assigned particular colors to facilitate cross-frame and cross-time point comparison of the same strut. Any suitable size metric can be used to quantify strut size and/or compare strut resorption over time.

For example, strut area, volume, and/or thickness can be measured. Given the pullback spacing between frames, the same exact struts may not be visible in the same frame in a follow-up pullback. For example, struts A and E were visible in the pullback performed after implant (FIG. 11A) but were not visible in the follow up image 9 months later (FIG. 11B). To compensate for missed struts, strut thickness can be measured over a given length (e.g., 0.5 mm, 1 mm, or the entire stent length), and the strut metric can be summed or averaged over the given length and subsequently used to quantify resorption.

Figure 12:
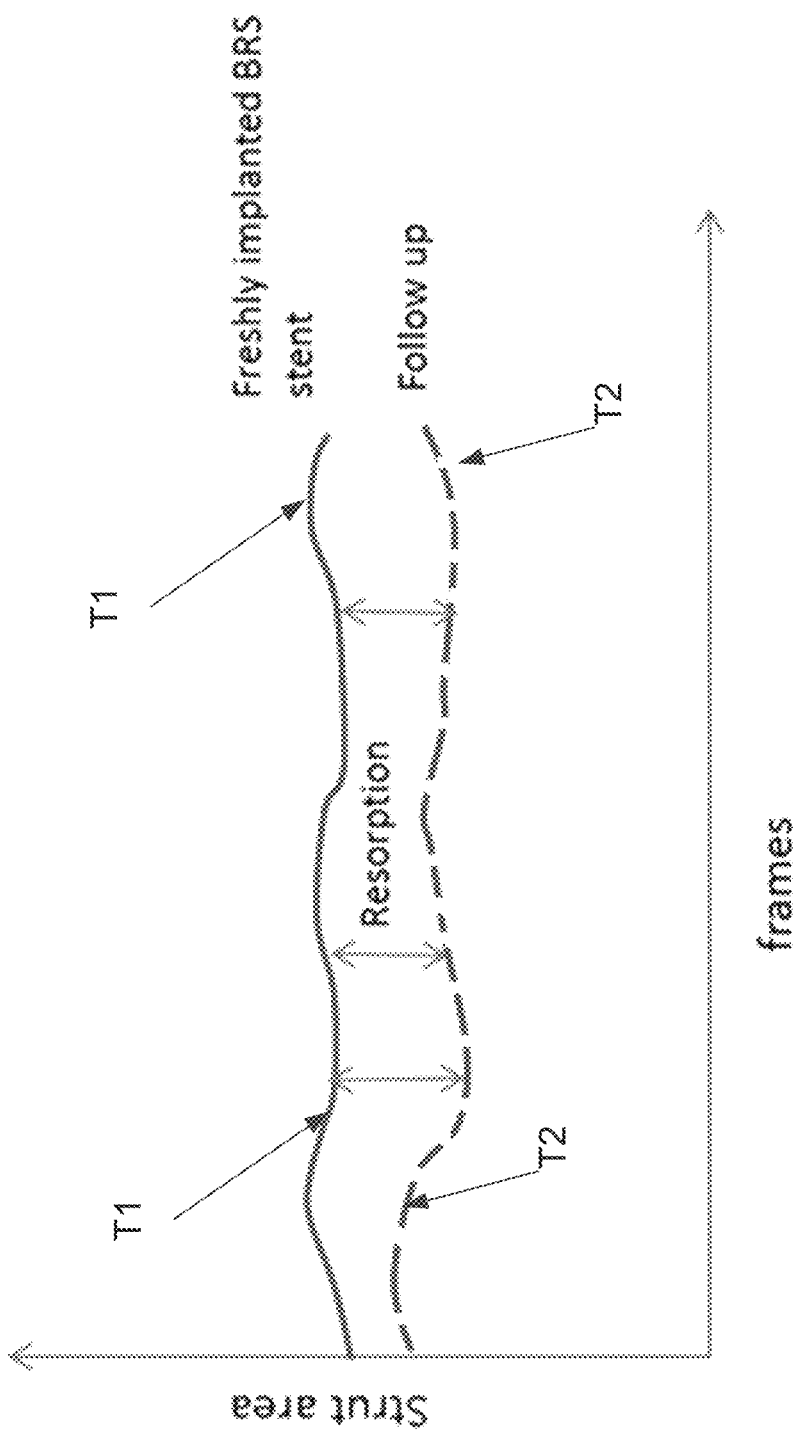
FIG. 12 is a graphical representation quantifying strut resorption at differing positions along a blood vessel between the time of implantation of BRS and a follow up visit according to an illustrative embodiment of the disclosure.

FIG. 12 is a graph quantifying strut resorption between the time of implantation of an absorbable endoprosthesis and a follow up visit. Endoprosthesis such as BRS, for example, are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

As shown in FIG. 12, strut area per frame along a length of BRS is measured soon after implant at time T1 and again at a later time T2 during a follow up pullback. T2 is greater than T1. For example, the time period between T1 and T2 can be hours, days, months, years, or combinations thereof. The difference R between the curves indicates the amount of resorption at each region of the vessel. Along the frames, which span the length of the pullback through the vessel, the strut area at time T1 is greater and then decreases over time to reach the dotted line at time T2. This information, the difference measure R, can be displayed on various user interfaces such as those that display images of blood vessel and the validated BRS. In one embodiment, R is displayed on a per frame basis. In one embodiment, R is averaged or otherwise evaluated as a max R or min R or other statistical metric that considered R as it varies over time or position.

Various examples of suitable processing modules are discussed below in more detail. As used herein a module refers to software, hardware, or firmware suitable for performing a specific data processing or data transmission task. Typically, in a preferred embodiment a module refers to a software routine, program, or other memory resident application suitable for receiving, transforming, routing and processing instructions, or various types of data such as OCT scan data, user interface data, control signals, angiography data, user actions, frequencies, interferometer signal data, and other information of interest.

Software Features for Implementing Bioresorbable Device Detection, Analysis and Display The following description is intended to provide an overview of device hardware and other operating components suitable for performing the methods of the disclosure described herein. This description is not intended to limit the applicable environments or the scope of the disclosure. Similarly, the hardware and other operating components may be suitable as part of the apparatuses described above. The disclosure can be practiced with other system configurations, including personal computers, multiprocessor systems, microprocessor-based or programmable electronic device, network PCs, minicomputers, mainframe computers, and the like. The disclosure can also be practiced in distributed computing environments where tasks are performed by remote processing devices that are linked through a communications network such as in different rooms of a catheter or cath lab.

Some portions of the detailed description are presented in terms of algorithms and symbolic representations of operations on data bits within a computer memory. These algorithmic descriptions and representations can be used by those skilled in the computer and software related fields. In one embodiment, an algorithm is here, and generally, conceived to be a self-consistent sequence of operations leading to a desired result. The operations performed as methods stops or otherwise described herein are those requiring physical manipulations of physical quantities. Usually, though not necessarily, these quantities take the form of electrical or magnetic signals capable of being stored, transferred, combined, transformed, compared, and otherwise manipulated.

Unless specifically stated otherwise as apparent from the following discussion, it is appreciated that throughout the description, discussions utilizing terms such as "processing" or "computing" or "searching" or "detecting" or "measuring" or "calculating" or "comparing" "generating" or "identifying" or "sensing" or "determining" or "displaying," or Boolean logic or other set related operations or the like, refer to the action and processes of a computer system, or electronic device, that manipulates and transforms data represented as physical (electronic) quantities within the computer system's or electronic devices' registers and memories into other data similarly represented as physical quantities within electronic memories or registers or other such information storage, transmission or display devices.

The present disclosure, in some embodiments, also relates to apparatus for performing the operations herein. This apparatus may be specially constructed for the required purposes, or it may comprise a general purpose computer selectively activated or reconfigured by a computer program stored in the computer. Various circuits and components thereof can be used to perform some of the data collection and transformation and processing described herein.

The algorithms and displays presented herein are not inherently related to any particular computer or other apparatus. Various specialized intravascular data collection/imaging systems may be used with programs in accordance with the teachings herein. The required structure for a variety of these systems will appear from the description herein. In addition, the present disclosure is not described with reference to any particular programming language, and various embodiments may thus be implemented using a variety of programming languages.

Embodiments of the disclosure may be embodied in many different forms, including, but in no way limited to, computer program logic for use with a processor (e.g., a microprocessor, microcontroller, digital signal processor, or general purpose computer), programmable logic for use with a programmable logic device, (e.g., a Field Programmable Gate Array (FPGA) or other programmable logic device), discrete components, integrated circuitry (e.g., an Application Specific Integrated Circuit (ASIC)), or any other means including any combination thereof. In a typical embodiment of the present disclosure, some or all of the processing of the data collected using an OCT probe and the processor-based system is implemented as a set of computer program instructions that is converted into a computer executable form, stored as such in a computer readable medium, and executed by a microprocessor under the control of an operating system.

Thus, query, response, transmitted probe data, input data and other data and signal described herein are transformed into processor understandable instructions suitable for detecting BRS, detecting malapposition of BRS relative to a vessel wall, detection absorption changes of a BRS, displaying and plotting data and parameters as described herein such in regions of a GUI and otherwise performing analysis and comparisons based on BRS changes over time, and other features and embodiments described above. Data and parameters suitable for display as plotted curve, values, or as another representation in a graphical user interface can include without limitation BRS position, absorption changes over time, OCT images of a blood vessel with BRS, malapposition of BRS, and other BRS related data sets.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Various examples of suitable processing modules are discussed below in more detail. As used herein a module refers to software, hardware, or firmware suitable for performing a specific data processing or data transmission task. Typically, in a preferred embodiment a module refers to a software routine, program, or other memory resident application suitable for receiving, transforming, routing and processing instructions, or various types of data such as filters, intensity variations from a BRS, BRS inner regions, BRS outer borders, boundary of strut endfaces, and other information of interest.

Computers and computer systems described herein may include operatively associated computer-readable media such as memory for storing software applications used in obtaining, processing, storing and/or communicating data. It can be appreciated that such memory can be internal, external, remote or local with respect to its operatively associated computer or computer system.

Memory may also include any means for storing software or other instructions including, for example and without limitation, a hard disk, an optical disk, floppy disk, DVD (digital versatile disc), CD (compact disc), memory stick, flash memory, ROM (read only memory), RAM (random access memory), DRAM (dynamic random access memory), PROM (programmable ROM), EEPROM (extended erasable PROM), and/or other like computer-readable media.

In general, computer-readable memory media applied in association with embodiments of the disclosure described herein may include any memory medium capable of storing instructions executed by a programmable apparatus. Where applicable, method steps described herein may be embodied or executed as instructions stored on a computer-readable memory medium or memory media. These instructions may be software embodied in various programming languages such as C++, C, Java, and/or a variety of other kinds of software programming languages that may be applied to create instructions in accordance with embodiments of the disclosure.

The term "machine-readable medium" or "computer-readable-medium" includes any medium that is capable of storing, encoding or carrying a set of instructions for execution by the machine and that cause the machine to perform any one or more of the methodologies of the present disclosure. While the machine-readable medium is shown in an example embodiment to be a single medium, the term "machine-readable medium" should be taken to include a single medium or multiple media (e.g., a database, one or more centralized or distributed databases and/or associated caches and servers) that store the one or more sets of instructions.

A storage medium may be non-transitory or include a non-transitory device. Accordingly, a non-transitory storage medium or non-transitory device may include a device that is tangible, meaning that the device has a concrete physical form, although the device may change its physical state. Thus, for example, non-transitory refers to a device remaining tangible despite this change in state.

The aspects, embodiments, features, and examples of the disclosure are to be considered illustrative in all respects and are not intended to limit the disclosure, the scope of which is defined only by the claims. Other embodiments, modifications, and usages will be apparent to those skilled in the art without departing from the spirit and scope of the claimed disclosure.

The use of headings and sections in the application is not meant to limit the disclosure; each section can apply to any aspect, embodiment, or feature of the disclosure.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself ±10%, unless specifically stated otherwise.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the disclosure as if each value were specifically enumerated herein. In addition, smaller ranges between and including the upper and lower limits of a given range are contemplated and encompassed within the disclosure. The listing of exemplary values or ranges is not a disclaimer of other values or ranges between and including the upper and lower limits of a given range.

It is to be understood that the figures and descriptions of the disclosure have been simplified to illustrate elements that are relevant for a clear understanding of the disclosure, while eliminating, for purposes of clarity, other elements. Those of ordinary skill in the art will recognize, however, that these and other elements may be desirable. However, because such elements are well known in the art, and because they do not facilitate a better understanding of the disclosure, a discussion of such elements is not provided herein. It should be appreciated that the figures are presented for illustrative purposes and not as construction drawings. Omitted details and modifications or alternative embodiments are within the purview of persons of ordinary skill in the art.

It can be appreciated that, in certain aspects of the disclosure, a single component may be replaced by multiple components, and multiple components may be replaced by a single component, to provide an element or structure or to perform a given function or functions. Except where such substitution would not be operative to practice certain embodiments of the disclosure, such substitution is considered within the scope of the disclosure.

The examples presented herein are intended to illustrate potential and specific implementations of the disclosure. It can be appreciated that the examples are intended primarily for purposes of illustration of the disclosure for those skilled in the art. There may be variations to these diagrams or the operations described herein without departing from the spirit of the disclosure. For instance, in certain cases, method steps or operations may be performed or executed in differing order, or operations may be added, deleted or modified.

What is claimed is:

1. A method of detecting a bioresorbable scaffold in a blood vessel comprising:
   storing, in an electronic memory storage device, intravascular image data from a pullback of an intravascular probe through the blood vessel and a bioresorbable scaffold disposed in the blood vessel, the bioresorbable scaffold having one or more struts;
   generating a plurality of image frames from the stored intravascular image data, the stored intravascular image data comprising a plurality of scan lines;
   generating a mask for one or more image frames of the plurality of image frames;
   inverting the mask to generate an inverted mask, wherein the inverted mask comprises bright pixel regions separated by dark pixel regions;
   detecting a group of bright pixel regions;
   identifying the group of bright pixel regions as defining a candidate inner region of a strut of the bioresorbable scaffold; and
   detecting a plurality of zero crossing regions in an image frame or in the inverted mask and excluding one or more candidate inner regions if zero crossing regions are not disposed on two or more sides of a candidate inner region of a strut.

2. The method of claim 1 wherein groupings of the bright pixel regions define a plurality of insular regions separated by a plurality of the dark pixel regions.

3. The method of claim 1 wherein the dark pixel regions correspond to background and bright pixel regions correspond to foreground.

4. The method of claim 1 wherein detecting the group of bright pixel regions comprises performing multiresolution filtering using a first filter and a second filter, wherein the first filter and the second filter are morphological filters.

5. The method of claim 1 wherein detecting a group of bright pixel regions is performed on a shape-independent basis, such that boxes or edges are not used to identify the group of bright pixel regions.

6. The method of claim 1 further comprising validating a plurality of detected struts and displaying the validated struts relative to a graphic user interface of an intravascular imaging system.

7. The method of claim 1 further comprising
   determining a strut end face boundary and
   determining a lumen boundary of the blood vessel.

8. The method of claim 7 further comprising
   determining a separation distance D using the determined lumen boundary and the strut end face boundary.

9. The method of claim 1 further comprising detecting a guidewire shadow, detecting a lumen boundary, and detecting a side branch shadow.

10. The method of claim 1 further comprising scanning on a per pixel basis and comparing each pixel relative to a local neighborhood thereof to determine if a given pixel is a local intensity maxima.

11. The method of claim 1 further comprising
    measuring a size attribute of at least one strut at a first point in time;
    measuring a size attribute of the at least one strut at a second point in time; and
    calculating a change in the size attribute between the first time and the second time.

12. The method of claim 1 wherein the plurality of image frames are optical coherence tomography images generated from a plurality of scan lines.

13. The method of claim 1 further comprising filtering, using a Laplacian of a Gaussian filter, the inverted mask to identify one or more interior strut regions.

14. The method of claim 1 wherein one or more of the step of generating a mask, the step of inverting the mask, and the step of detecting a group of bright pixel regions are performed by an image processing module of an intravascular data collection system in electronic communication with the electronic memory storage device.

15. A method of detecting a bioresorbable device in a blood vessel, the method comprising:
    converting an image of a blood vessel to an image mask, the image comprising struts of a bioresorbable scaffold;

inverting the image mask to create an inverted image mask, detecting an insular group of bright pixels;

filtering the insular group of bright pixels using one or more morphological filters to identify candidate struts; and validating the candidate struts to identify one or more struts of the bioresorbable scaffold by performing a zero crossing analysis to eliminate luminous interior strut regions that are not bounded by a zero crossing detection on all sides.

16. The method of claim 15, further comprising filtering the inverted image mask to identify local intensity maxima in one or more interior strut regions, wherein clusters of local intensity maxima correspond to the location of individual struts in the image.

17. The method of claim 16, further comprising combining a location of the one or more interior strut regions of the insular group with a location of local intensity maxima clusters.

18. The method of claim 15 further comprising generating the image using in vivo measurements obtained using an intravascular imaging probe.

19. The method of claim 15 wherein one or more of the step of converting an image, the step of inverting the image mask, and the step of detecting an insular group of bright pixels are performed by an image processing module of an intravascular data collection system.

20. The method of claim 19 further comprising displaying the validated struts relative to a graphic user interface of an intravascular imaging system.

21. A system for detecting a bioresorbable device having struts in a blood vessel, the system comprising:

one or more memory devices; and a computing device in communication with the memory device, wherein the memory device comprises instructions executable by the computing device to cause the computing device to generate a plurality of image frames from intravascular image data stored in the memory device;

generate a binary mask for the plurality of image frames;

identify inner regions of a first intensity level in each binary mask;

identify border regions of a second intensity level in each binary mask;

identify one or more candidate struts based on a per frame basis based on relative position of one inner region relative to one or more border regions; and filter the one or more candidate struts to exclude candidates if zero crossing regions are not disposed on two or more sides of a candidate strut.

22. The system of claim 21 further comprising instructions to cause the computing device to determine a strut end face boundary.

23. The system of claim 22 further comprising instructions to cause the computing device to determine a stent or scaffold separation distance D using a detected lumen boundary and the strut end face boundary.

24. The system of claim 21 further comprising instructions to cause the computing device to display a separation distance D on a graphical user interface of an imaging system.

* * * * *